US012128057B2

(12) United States Patent
Bucci et al.

(10) Patent No.: US 12,128,057 B2
(45) Date of Patent: *Oct. 29, 2024

(54) DIETARY NUTRIENT COMPOSITIONS

(71) Applicant: Natals, Inc., Culver City, CA (US)

(72) Inventors: Luke Bucci, Reno, NV (US); Katerina Schneider, Los Angeles, CA (US); Mastaneh Sharafi, Redondo Beach, CA (US); Nima Alamdari, Los Angeles, CA (US)

(73) Assignee: NATALS, INC., Culver City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/840,332

(22) Filed: Jun. 14, 2022

(65) Prior Publication Data

US 2022/0305033 A1 Sep. 29, 2022

Related U.S. Application Data

(63) Continuation of application No. 17/365,949, filed on Jul. 1, 2021, which is a continuation of application No. 15/719,127, filed on Sep. 28, 2017, now Pat. No. 11,083,738.

(51) Int. Cl.
| | | |
|---|---|---|
| *A61K 31/593* | (2006.01) |
| *A23D 9/007* | (2006.01) |
| *A23L 5/00* | (2016.01) |
| *A23L 33/00* | (2016.01) |
| *A23L 33/115* | (2016.01) |
| *A23L 33/12* | (2016.01) |
| *A23L 33/15* | (2016.01) |
| *A23L 33/155* | (2016.01) |
| *A23L 33/16* | (2016.01) |
| *A61K 9/16* | (2006.01) |
| *A61K 9/48* | (2006.01) |
| *A61K 31/122* | (2006.01) |
| *A61K 31/202* | (2006.01) |
| *A61K 31/355* | (2006.01) |
| *A61K 31/519* | (2006.01) |
| *A61K 31/714* | (2006.01) |
| *A61K 33/06* | (2006.01) |
| *A61K 33/22* | (2006.01) |
| *A61K 33/26* | (2006.01) |
| *A61K 36/02* | (2006.01) |
| *A61K 36/31* | (2006.01) |
| *B65D 25/54* | (2006.01) |
| *B65D 81/20* | (2006.01) |

(52) U.S. Cl.
CPC ............ *A61K 31/593* (2013.01); *A23D 9/007* (2013.01); *A23L 5/00* (2016.08); *A23L 33/115* (2016.08); *A23L 33/12* (2016.08); *A23L 33/15* (2016.08); *A23L 33/155* (2016.08); *A23L 33/16* (2016.08); *A23L 33/40* (2016.08); *A61K 9/1652* (2013.01); *A61K 9/1664* (2013.01); *A61K 9/1676* (2013.01); *A61K 9/4808* (2013.01); *A61K 31/122* (2013.01); *A61K 31/202* (2013.01); *A61K 31/355* (2013.01); *A61K 31/519* (2013.01); *A61K 31/714* (2013.01); *A61K 33/06* (2013.01); *A61K 33/22* (2013.01); *A61K 33/26* (2013.01); *A61K 36/02* (2013.01); *A61K 36/31* (2013.01); *B65D 25/54* (2013.01); *B65D 81/2076* (2013.01); *A23V 2002/00* (2013.01); *B65D 2203/12* (2013.01)

(58) Field of Classification Search
CPC .. A61K 31/593; A61K 9/1652; A61K 9/1664; A61K 9/1676; A61K 9/4808; A61K 31/122; A61K 31/202; A61K 31/355; A61K 31/519; A61K 31/714; A61K 33/06; A61K 33/22; A61K 33/26; A61K 36/02; A61K 36/31; A23L 33/12; A23L 33/15; A23L 33/155; A23L 33/16; A23L 33/40; B65D 25/54; B65D 81/2076; B65D 2203/12; A23V 2002/00
See application file for complete search history.

(56) References Cited

U.S. PATENT DOCUMENTS

| | | | |
|---|---|---|---|
| 2,421,598 A | 6/1947 | Buxton et al. |
| 5,654,011 A | 8/1997 | Jackson et al. |
| 6,451,341 B1 | 9/2002 | Slaga et al. |
| 6,488,956 B1 | 12/2002 | Paradissis et al. |
| 7,994,217 B2 | 8/2011 | Nidamarty et al. |
| 8,183,227 B1 * | 5/2012 | Perrin .................. A61K 31/715 514/276 |

(Continued)

FOREIGN PATENT DOCUMENTS

| | | | | |
|---|---|---|---|---|
| BR | PI0712566 | * | 1/2013 | |
| CA | 2551650 A1 | * | 1/2007 | ............... B32B 7/02 |

(Continued)

OTHER PUBLICATIONS

CA 2551650A1 Translation.*
BR PI0712566 Translation.*
JP 2012-529902 Translation.*
Alaimo, K. et al. (1994). Dietary intake of vitamins, minerals, and fiber of persons ages 2 months and over in the United States: Third National Health and Nutrition Examination Survey, Phase 1, 1988-1991.
Adami, S. et al. (2008). "Relationship between serum parathyroid hormone, vitamin D sufficiency, age, and calcium intake," *Bone* 42:267-270.

(Continued)

*Primary Examiner* — Snigdha Maewall
(74) *Attorney, Agent, or Firm* — COOLEY LLP

(57) ABSTRACT

Provided herein are dietary supplement compositions comprising a plurality of beadlets and an oil. Provided herein are also dietary supplement compositions comprising a plurality of mini-tabs and oil. The beadlets or mini-tabs comprise at least one nutrient that is miscible in aqueous solution, and the oil comprises at least one fat-soluble nutrient. The composition may be contained within one or more capsules, and be packaged with a scented insert.

33 Claims, No Drawings

(56) References Cited

U.S. PATENT DOCUMENTS

| | | | |
|---|---|---|---|
| 8,377,471 | B2 | 2/2013 | Vanquickenborne et al. |
| 8,389,504 | B2 | 3/2013 | Debbouz et al. |
| 8,852,631 | B2 | 10/2014 | Cade et al. |
| 9,072,693 | B2 | 7/2015 | Thys-Jacobs |
| 10,617,700 | B1 * | 4/2020 | Toothman ............... A61P 3/02 |
| 11,083,738 | B2 | 8/2021 | Bucci et al. |
| 2003/0206969 | A1 | 11/2003 | Nidamarty et al. |
| 2004/0001817 | A1 | 1/2004 | Giampapa |
| 2004/0213857 | A1 | 10/2004 | Soldati et al. |
| 2007/0029400 | A1 | 2/2007 | Magargee et al. |
| 2010/0129496 | A1 | 5/2010 | Kirschner et al. |
| 2011/0312927 | A1 | 12/2011 | Nachaegari et al. |
| 2013/0017182 | A1 | 1/2013 | Lukina |
| 2013/0095189 | A1 * | 4/2013 | Jouni ................. A23L 33/105 514/5.5 |
| 2013/0287842 | A1 | 10/2013 | Cade et al. |
| 2014/0364491 | A1 * | 12/2014 | Bortz .................. A61K 45/06 514/494 |
| 2015/0050261 | A1 * | 2/2015 | Evenstad ............ A61K 31/519 424/94.1 |
| 2015/0343009 | A1 | 12/2015 | Igarashi et al. |
| 2017/0112178 | A1 * | 4/2017 | Perrin ................. A61K 31/593 |
| 2018/0368458 | A1 * | 12/2018 | White .................. A61K 9/1676 |
| 2022/0096499 | A1 | 3/2022 | Bucci et al. |
| 2022/0226352 | A1 | 7/2022 | Bucci et al. |
| 2022/0305033 | A1 | 9/2022 | Bucci et al. |

FOREIGN PATENT DOCUMENTS

| | | |
|---|---|---|
| CN | 103446340 A | 12/2013 |
| DE | 202015100275 U1 | 3/2015 |
| EP | 1 617 734 A1 | 1/2006 |
| GB | 1059578 A | 2/1967 |
| JP | 2012-529902 * | 10/2014 |
| WO | WO-01/43571 A1 | 6/2001 |
| WO | WO-2008/117682 A1 | 10/2008 |
| WO | WO-2014/032742 A1 | 3/2014 |

OTHER PUBLICATIONS

Bellamins (2018). 1$^{st}$ Trimester Blend—Premium Prenatal Vitamin Drink Mix, berry-lemonade 30 day supply, 3 total pages.
Bellamins (2018). 2$^{nd}$ Trimester Blend—Premium Prenatal Vitamin Drink Mix, berry-lemonade 30 day supply, 3 total pages.
Bellamins (2018). 3$^{rd}$ Trimester Blend—Premium Prenatal Vitamin Drink Mix, berry-lemonade 30 day supply, 3 total pages.
Buhr, S. (2016). "Ritual wants to reinvent the vitamin," Disrupt NY 2016, TechCrunch, located at https://techcrunch.com/2016/05/10/ritual-wants-to-reinvent-the-vitamin/, 8 total pages.
Daily Value Reference of the Dietary Supplement Label Database (DSLD), 2016, 4 total pages.
Dietary Guidelines for Americans (2015-2020). Eighth Edition, 144 total pages.
Emerald (2018). Prenatal 1-daily Multi, 6 total pages.
English, N. (2020). "Ritual's Essential Multivitamin for Men—Extra Absorbable Nutrients?" Located at https://barbend.com/ritual-mens-multivitamin-review/, 14 total pages.
Final Office Action mailed on Aug. 31, 2020, for U.S. Appl. No. 15/719,127, filed on Sep. 28, 2017, 11 pages.
Fitzpatrick, C. (2020). "Ritual just launched Multivitamins for Men to fill the nutrient gaps in their diets," Located at https://www.bestproducts.com/fitness/a33013445/ritual-essential-for-men-multivitamins/, 3 total pages.
Fulgoni III, V.L. (2011). "Foods, fortificants, and supplements: Where do Americans get their nutrients?" J. Nutrition 141:1847-1854.
Garden of Life Mykind Organics Women's Multi Vitamin (2014). 2 total pages.
Igennus.com (2016). Avoiding omega-3 deficiency, 4 total pages.
Institute of Medicine (US) Panel on Micronutrients (2001). Dietary Reference Intakes for Vitamin A, Vitamin K, Arsenic, Boron, Chromium, Copper, Iodine, Iron, Manganese, Molybdenum, Nickel, Silicon, Vanadium, and Zinc. Washington (DC): National Academies Press (US), Chapter 12: Zinc, 50 total pages.
International Search Report mailed on Dec. 7, 2018, for PCT Application No. PCT/US2018/053460, filed on Sep. 28, 2018, 3 pages.
Jarrow Formulas (2017). Ultra Bone-Up. 2 total pages.
Lamborn, C. (2020). "My Ritual Essential for men review—Is it worth trying?" located at https://www.mysubscriptionaddiction.com/ritual-for-men-review, 9 total pages.
Life Extension (2016). Two-Per-Day Tablets, 5 total pages.
Life Extension (2018). Vitamins D and K with Sea-Iodine and Vitamin K2, 3 total pages.
Lindberg (2018). Pink Women's Multi 1 with Iron, 4 total pages.
Lips, P. et al. (2001). "A global study of vitamin D status and parathyroid function in postmenopausal women with osteoporosis: baseline data from the multiple outcomes of raloxifene evaluation clinical trial," *JCE & M* 86:1212-1221.
Liu, R.H. (2003). "Health benefits of fruit and vegetables are from additive and synergistic combinations of phytochemicals," *Am. J. Clin. Nutr.* 78(Suppl):517S-520S.
Menayang, A. (2017). "Ritual ushers in the age of transparent and 'instagramable' supplements," Located at https://www.nutraingredients-usa.com/Article/2017/02/14/Ritual-ushers-in-the-age-of-transparent-and-instagramable-supplements, 5 total pages.
Mercola (2013). "Beyond calcium and vitamin D—How to really build strong bones," Peak Fitness presented by Mercola.com, 5 total pages.
Mithal, A. et al. (2009). "Global vitamin D status and determinants of hypovitaminosis D," *Osteo. Int.* 20:1807-1820.
Mogosanu, G.D. et al. (2016). "Calcium Fructoborate for Bone and Cardiovascular Health," Biol. Trace Elem. Res. 172:277-281.
Morning Pep (2018). Prenatal Vitamins, 1 total page.
National Institutes of Health (2021). Vitamin B12—Fact Sheet for Health Professionals, located at https://ods.od.nih.gov/factsheets/VitaminB12-HealthProfessional/, 21 total pages.
National Institutes of Health (2021). Vitamin K—Fact Sheet for Health Professionals, located at https://ods.od.nih.gov/factsheets/VitaminK-HealthProfessional/, 15 total pages.
New Chapter Women's Wellness (2018). Every Woman's One Daily Multivitamin, 12 total pages.
Newnham, R.E. (1994). "Essentiality of boron for healthy bones and joints," *Environ. Health Perspectives* 102(Suppl 7):83-85.
Non-Final Office Action mailed on May 16, 2019, for U.S. Appl. No. 15/719,127, filed on Sep. 28, 2017, 7 pages.
Non-Final Office Action mailed on Nov. 29, 2019, for U.S. Appl. No. 15/719,127, filed on Sep. 28, 2017, 8 pages.
Notice of Allowance mailed on Apr. 14, 2021, for U.S. Appl. No. 15/719,127, filed on Sep. 28, 2017, 9 pages.
Pocobelli, G. et al. (2009). "Use of supplements of multivitamins, vitamin C, and vitamin E in relation to mortality," *Am. J. Epidemiology* 170:472-483.
Paleohacks (2017). Welcome to Paleohacks. Located at https://www.paleohacks.com/, 3 total pages.
Pomegranate Liquid Multivitamins: Vitamins A, B, C, D, E, K and mineral supplement. Superfood—super absorption (2018). 7 total pages.
Pure Encapsulations (2015). Product information sheet—Multi t/d with Metafolin® L-5 MTHF introduced 2005, 2 total pages.
Pure Encapsulations (2018). Nutrient 950® with Vitamin K, 5 total pages.
Reflex Nutrition (2018). Nexgen Pro Sports Multivitamin, 2 total pages.
Ritual Ingredients (2018). Overview. Located at https://ritual.com/pages/ingredients, 7 total pages.
SmartyPants Prenatal Women's Complete (2016). 18 total pages.
SmartyPants PreNatal Gummy Multivitamin, 180 count (2015). 14 total pages.
Strom, S. (2016). "Vitamins join the 'clean label' bandwagon," The New York Times—Business Day, located at https://www.nytimes.com/2016/05/27/business/vitamins-join-the-clean-label-bandwagon.html, 4 total pages.

(56) References Cited

OTHER PUBLICATIONS

Swanson (2018). Super Nutrition Simply One 50+ Women Triple Power, 6 total pages.
TechCrunch (2016). Startup Battlefield: Ritual at #TCDisrupt, located at https://twitter.com/TechCrunch/status/730140878245928960, Twitter video.
Tespo (2016). Women's Essential—31 serving per disc, 2 total pages.
Thorne (2018). Multi-Vitamin Elite, 9 total pages.
Thorne (2018). AI's Formula for Men, 7 total pages.
Thorne (2018). Basic Nutrients 2/day, 7 total pages.
Tsang, B.L. et al. (2015). "Assessing the association between the methylenetetrahydrofolate reductase (MTHFR) 677C>T polymorphism and blood folate concentrations: a systematic review and meta-analysis of trials and observational studies," Am. J. Clin. Nutr. 101:1286-1294.
USDA (2015-2016). What We Eat in America, NHANES 2015-2016, Tables, 160 total pages.
USDA (2013-2016). Usual Nutrient Intake from Food and Beverages, by Gender and Age, What We Eat in America, NHANES 2013-2016, 52 total pages.
Vitacost Synergy (2018). Twice Daily Energy Plus Multi-Vitamin, 5 total pages.
Wartella, E.A. et al. (2010). "Front-of-Package Nutrition Rating Systems and Symbols—Phase I Report," Institute of Medicine of the National Academies, pp. 1-128.
WHO (2008). "Interim Summary of Conclusions and Dietary Recommendations on Total Fat & Fatty Acids," From the Joint FAO/WHO Expert Consultation on Fats and Fatty Acids in Human Nutrition, Nov. 10-14, 2008, WHO, Geneva, 14 total pages.
Written Opinion of the International Searching Authority mailed on Dec. 7, 2018, for PCT Application No. PCT/US2018/053460, filed on Sep. 28, 2018, 6 pages.
Zhou, B.F. et al. (2003). "Nutrient intakes of middle-aged men and women in China, Japan, United Kingdom, and United States in the late 1990s: The Intermap Study," J. Human Hypertension 17:623-630.
Non-Final Office Action mailed on Jun. 24, 2022, for U.S. Appl. No. 17/715,634, filed Apr. 7, 2022, 15 pages.
Final Office Action mailed on Mar. 22, 2023, for U.S. Appl. No. 17/715,634, filed Apr. 7, 2022, 16 pages.
Final Office Action mailed on Jun. 7, 2023, for U.S. Appl. No. 17/365,949, filed Jul. 1, 2021, 16 pages.
Non-Final Office Action mailed on Oct. 5, 2022, for U.S. Appl. No. 17/365,949, filed Jul. 1, 2021, 15 pages.
Non-Final Office Action mailed on Nov. 7, 2022, for U.S. Appl. No. 17/715,634, filed Apr. 7, 2022, 16 pages.
Non-Final Office Action mailed on Aug. 3, 2023, for U.S. Appl. No. 17/715,634, filed Apr. 7, 2022, 18 pages.
Non-Final Office Action mailed on Nov. 8, 2023, for U.S. Appl. No. 17/365,949, filed Jul. 1, 2021, 19 pages.
Final Office Action mailed on May 21, 2024, for U.S. Appl. No. 17/365,949, filed on Jul. 1, 2021, 8 pages.

* cited by examiner

DIETARY NUTRIENT COMPOSITIONS

CROSS-REFERENCE TO RELATED APPLICATIONS

This application is a continuation of U.S. patent application Ser. No. 17/365,949, filed Jul. 1, 2021, which is a continuation of U.S. patent application Ser. No. 15/719,127, filed on Sep. 28, 2017, now issued as U.S. Pat. No. 11,083,738, the subject matter of each of which is incorporated herein by reference in its entirety.

FIELD

The present disclosure relates generally to dietary supplements, and more specifically to dietary supplement compositions comprising two or more nutrients in separate phases.

BACKGROUND

The Daily values for nutrients listed on Food and Dietary Supplement Facts panels were established by the $7^{th}$ Revised Edition of Recommended Dietary Allowances Report by the United States National Research Council, Food and Nutrition Board, published in 1968. Recommended allowances (values) for some nutrients have changed in successive iterations of the Food and Nutrition Board meetings, but the Daily Values for many others have not changed.

The human studies used to determine these values were performed decades ago, primarily from balance studies and population intake averages, often without considering nutrient functionality, and when the role of certain nutrients and their metabolism by certain populations and individuals was not well understood. Thus, these values may not reflect the nutrient needs of certain human populations. Many multiple vitamin-mineral supplement products are unbalanced in view of modern human needs in that they oversupply certain nutrients and/or are deficient in others. Some supplements are produced using forms of nutrients based on stability or price, rather than what is most efficacious in the human body.

There have also been new observations about how the interplay of different nutrients, the presence of certain excipients, and the form of nutrients can affect nutrient absorption and/or metabolism. For example, Vitamin E exists in at least eight dietary forms. Specific Vitamin E binding proteins and receptors control Vitamin E metabolism, including formation of long-chain metabolites that can play a key role in Vitamin E functionality.

Finally, the diversity of nutrients is reflected in the diversity of their physical forms. It can be difficult to formulate a single supplement comprising nutrients miscible in aqueous solutions along with those that are fat-soluble. Combining solid nutrients with liquid nutrients can also be challenging. Those looking to consume a combination of nutrients often have to take an assortment of different tablets, capsules, powder, films, liquids, soft-gels, and/or gummy forms.

Thus, what is needed are nutrient supplements wherein the nutrients can be administered together, as one composition. In addition, what is needed are nutrient supplements which are formulated to comprise low levels, or are essentially free of, certain excipients.

BRIEF SUMMARY

In one aspect, provided herein is a dietary supplement which comprises a plurality of beadlets and oil, wherein:

the beadlets are solid, and comprise one or more nutrients miscible in aqueous solution selected from the group consisting of vitamin B12, boron, magnesium, iron, and folate; and the oil is liquid, and comprises one or more fat-soluble nutrients selected from the group consisting of vitamin K, vitamin D, vitamin E, and omega-3 fatty acids.

In some variations, the dietary supplement is a daily women's health dietary supplement. In some variations, the beadlets comprise boron and magnesium, and the oil comprises vitamin D and vitamin K. In other variations, the beadlets comprise vitamin B12, boron, magnesium, iron, and folate; and the oil comprises vitamin K, vitamin D, vitamin E, and omega-3 fatty acids.

In one aspect, provided herein is a dietary supplement wherein:

the beadlets comprise vitamin B12 as methylcobalamin, boron as calcium fructoborate, magnesium as a magnesium-sucrosome compound, iron as ferrous bisglycinate, and folate as (6S)-5-methyltetrahydrofolate glucosamine salt; and the oil comprises vitamin K as menaquinone-7, vitamin D3, vitamin E as mixed tocopherols, and the omega-3 fatty acids docosahexanoic acid and eicosapentaenoic acid.

In another aspect, provided herein is a dietary supplement wherein:

the beadlets consist essentially of methylcobalamin, calcium fructoborate, a magnesium-sucrosome compound, ferrous bisglycinate, (6S)-5-methyltetrahydrofolate glucosamine salt, cellulose, citric acid, corn starch, corn zein, dicalcium phosphate, tricalcium phosphate, lecithin, rice starch, and silica; and the oil consists essentially of menaquinone-7, vitamin D3, mixed tocopherols, algal oil comprising omega-3 fatty acids, ascorbyl palmitate, d-alpha-tocopherol, coconut oil, medium chain triglycerides, silica, sunflower oil, and one or more odorant agents.

In another aspect, provided herein is a dietary supplement wherein:

the beadlets consist essentially of methylcobalamin, calcium fructoborate, a magnesium-sucrosome compound, ferrous bisglycinate, (6S)-5-methyltetrahydrofolate glucosamine salt, cellulose, citric acid, corn starch, corn zein, tricalcium phosphate, lecithin, rice starch, and silica; and the oil consists essentially of menaquinone-7, vitamin D3, mixed tocopherols, algal oil comprising omega-3 fatty acids, ascorbyl palmitate, d-alpha-tocopherol, coconut oil, medium chain triglycerides, silica, sunflower oil, and one or more odorant agents.

In one variation, which may be combined with any of the preceding variations, the dietary supplement is a daily women's health dietary supplement. In some variations, the dietary supplement is packaged in a transparent bottle. In some variations, the bottle comprises a scented insert. In some variations, the scented insert comprises a polymer and a scented oil. In certain variations, the scented insert consists essentially of ethylene vinyl acetate and peppermint oil.

In some variations, each unit dose of the dietary supplement comprises between about 80 mcg to about 100 mcg vitamin K; between about 1800 IU to about 2200 IU vitamin D; between about 7 mcg to about 9 mcg vitamin B12; between about 0.9 mg to about 1.1 mg boron; between about 9 IU to about 11 IU of vitamin E; between about 45 mg to about 55 mg magnesium; between about 540 mcg to about 660 mcg of folate; between about 7 mg to about 9 mg iron; and between about 290 mg to about 350 mg of omega-3 fatty acids.

In some variations, each unit dose of the dietary supplement comprises between about 80 mcg to about 100 mcg vitamin K; between about 1800 IU to about 2500 IU vitamin D; between about 5 mcg to about 20 mcg vitamin B12; between about 0.9 mg to about 1.1 mg boron; between about 9 IU to about 15 IU of vitamin E; between about 35 mg to about 65 mg magnesium; between about 500 mcg to about 800 mcg of folate; between about 7 mg to about 9 mg iron; and between about 290 mg to about 350 mg of omega-3 fatty acids.

In some variations, which may be combined with any of the preceding variations, the daily women's health dietary supplement comprises vitamin D3, vitamin K, boron, and magnesium, and: the weight ratio of vitamin D3 to vitamin K is from about 0.045:0.099 to about 0.055:0.081; the weight ratio of vitamin K to boron is from about 0.081:1.1 to about 0.099:0.9; and the weight ratio of magnesium to boron is from about 45:1.1 to about 55:0.9.

DETAILED DESCRIPTION

The following description sets forth numerous exemplary configurations, methods, parameters, and the like. It should be recognized, however, that such description is not intended as a limitation on the scope of the present disclosure, but is instead provided as a description of exemplary embodiments.

Provided herein are dietary supplement compositions comprising a plurality of solid beadlets and oil, wherein the beadlets comprise at least one nutrient and the oil comprises at least one nutrient. Also provided herein are dietary supplement compositions comprising a plurality of solid mini-tabs and oil, wherein the mini-tabs comprise at least one nutrient and the oil comprises at least one nutrient. In some embodiments, the beadlets or mini-tabs comprise at least one nutrient that is miscible in aqueous solution, and the oil comprises at least one nutrient that is fat-soluble. In certain embodiments, the oil is liquid. Thus, provided herein are compositions comprising a plurality of solid beadlets and oil, wherein the beadlets comprise at least one nutrient, the oil comprises at least one nutrient, and the beadlets and oil form a heterogeneous mixture. Provided herein are also compositions comprising a plurality of solid mini-tabs and oil, wherein the mini-tabs comprise at least one nutrient, the oil comprises at least one nutrient, and the mini-tabs and oil form a heterogeneous mixture. In certain embodiments, the compositions provided herein allow for the delivery of both fat-soluble and aqueous-miscible nutrients together in one mixture. This may avoid, for example, the requirement of separate capsules or tablets to deliver a combination of nutrients to a subject.

In certain embodiments, the dietary supplement is contained within a capsule shell. In some embodiments, the capsule shell delays release of the oil and beadlets, or oil and mini-tabs, until the composition has passed through the stomach of a mammal. In some embodiments, the mammal is a human. The capsule shell may be essentially free of components derived from animals.

I. Definitions

The term "nutrient" as used herein refers to any nutritional or dietary supplement including but not limited to vitamins, minerals, amino acids, probiotics, or fatty acids, or concentrates, metabolites, constituents, or combinations of the same.

The term "unit dose" or "unit dosage" means a dosage form containing an amount of the composition described herein in one single dose. The unit dose may be, for example, in the form of one or more capsules.

II. Beadlet

Provided herein are dietary supplement compositions comprising a plurality of solid beadlets, which comprise a core and one or more coatings. At least one of the one or more coatings comprises at least one nutrient miscible in an aqueous solution. Thus, the beadlets comprise at least one nutrient miscible in an aqueous solution. In some embodiments, nutrients miscible in aqueous solution include those that are soluble in aqueous solution, will suspend in aqueous solution, or will dissolve in aqueous solution as a salt, or any combinations thereof. In some embodiments, the beadlets comprise at least one nutrient soluble in an aqueous solution, for example wherein at least one of the one or more coatings of the beadlets comprises at least one nutrient soluble in an aqueous solution. In certain embodiments, the beadlets comprise one or more nutrients that are soluble in the gastrointestinal tract of a mammal. The beadlets may comprise one or more nutrients that are soluble in the small intestine of a mammal, the large intestine of a mammal, or both. In some embodiments, the beadlets comprise one or more nutrients that are soluble in the small intestine of a mammal. In some embodiments, the mammal is a human. The one or more nutrients may be, for example, vitamins or dietary minerals, or combinations thereof.

A. Core

Each beadlet comprises a core. The core may be any suitable shape. For example, the core may be generally spherical in shape, or generally ovoid in shape. In some embodiments, the core is a sphere. In other embodiments, the core is an ovoid. The core comprises a solid material. In certain embodiments, the core comprises cellulose, such as microcrystalline cellulose (MCC). In some embodiments, the core is essentially free of disaccharides, essentially free of monosaccharides, or essentially free of both disaccharides and monosaccharides. In some embodiments, the core is essentially free of glucose, fructose, galactose, mannose, arabinose, erythrose, and allose. In other embodiments, the core is essentially free of sucrose, lactose, lactulose, and maltose. In certain embodiments, the core is essentially free of glucose, fructose, galactose, mannose, arabinose, erythrose, allose, sucrose, lactose, lactulose, and maltose. In one embodiment, the core is essentially free of sucrose.

B. Coating

Each beadlet comprises one or more coating layers surrounding the core, wherein at least one of the one or more coating layers is a nutrient layer comprising a nutrient miscible in an aqueous solution. In some embodiments, least one of the one or more coating layers is a nutrient layer comprising a nutrient soluble in an aqueous solution. In some embodiments, the beadlet comprises a plurality of nutrient layers. For example, a beadlet may comprise a first nutrient layer surrounding the core, and a second nutrient layer surrounding the first nutrient layer.

The one or more nutrient layers may independently comprise at least one nutrient. Each nutrient layer may independently comprise a single nutrient, or a plurality of nutrients. Thus, for example, in certain embodiments the beadlet comprises a core, an initial nutrient layer comprising a plurality of nutrients surrounding the core, and an additional nutrient layer comprising one nutrient surrounding the first nutrient layer.

The one or more coating layers may independently comprise one or more excipients, for example one or more binders, fillers, diluents, lubricants, or any combination thereof. In certain embodiments, the excipient is selected from the group consisting of cellulosic material, citric acid, starch, protein, alginate, calcium phosphate salts (such as tricalcium phosphate and dicalcium phosphate), lecithin, and silica. In some embodiments, the cellulosic material is microcrystalline cellulose (MCC). The starch may be corn starch, rice starch, pea starch, tapioca starch, or a combination thereof. In some embodiments, the starch is pregelatinized. In some embodiments, the excipient is a vegetable gum, or mixture of vegetable gums. In certain embodiments, the protein is zein, such as corn zein. The one or more excipients may include one or more excipients combined with a nutrient to form a coating layer; or one or more excipients associated with one or more nutrients as a nutrient compound; or any combinations thereof.

In certain embodiments, the beadlets comprise at least one nutrient layer that comprises one or more excipients. In some embodiments, the beadlets comprise a coating layer that consists essentially of an excipient. The coating layer may comprise up to 95 wt %, up to 98 wt %, up to 99 wt %, up to 99.5 wt %, up to 99.9 wt %, or up to 99.99 wt % of one or more excipients. In one embodiment, the coating layer comprises zein, such as corn zein.

In some embodiments, the outer-most layer of the beadlets is a coating layer that does not comprise a nutrient, such as a vitamin, probiotic, dietary mineral, or fatty acid. The outer coating may help maintain the heterogeneous mixture of the beadlets in the oil, and may prevent the nutrients coating the beadlet core from contacting the oil. Separating certain nutrients by using the beadlet-in-oil compositions described herein may help maintain the stability and activity of certain nutrients, which in turn may improve absorption and/or activity in the body. For example, iron salt may interact with and negatively impact the potency of vitamin D3, vitamin E, vitamin B12, DHA and EPA. In compositions comprising two or more of these nutrients, locating the iron in the solid beadlets and one or more of the other nutrients in the oil may prevent or reduce interactions between iron and the other nutrients.

In certain embodiments, the outer layer comprises a protein, such as corn zein. In some embodiments, the outer layer consists essentially of a protein, such as corn zein. The corn zein may, in some embodiments, be derived from corn that has not been genetically modified.

In certain embodiments, one or more coating layers, including one or more nutrient layers, of the beadlets are essentially free of certain excipients. For example, the one or more coating layers of the beadlets may be essentially free of titanium (such as titanium dioxide), polymers synthesized from petroleum or petroleum products, polyvinylpyrrolidine, polyethylene glycols, talc, disaccharides (such as sucrose), or lac resin (shellac), or any combinations thereof. In certain embodiments, the beadlets comprise less than 0.1 wt %, less than 0.01 wt %, less than 0.001 wt %, or less than 0.0001 wt % of titanium (such as titanium dioxide), polymers synthesized from petroleum or petroleum products, polyvinylpyrrolidine, polyethylene glycols, talc, disaccharides (such as sucrose), or lac resin (shellac), or any combinations thereof.

In certain embodiments, one or more coating layers, including one or more nutrient layers, of the beadlets are essentially free of artificial colorants. For example, the one or more coating layers of the beadlets may be essentially free of FD&C Blue No. 1, FD&C Blue No. 2, FD&C Green No. 3, FD&C Yellow No. 5 (tartrazine), FD&C Yellow No. 6, or FD&C Red No. 3, FD&C Red No. 40, or the lake pigments of any of these, or any combinations thereof. In certain embodiments, the beadlets comprise less than 0.1 wt %, less than 0.01 wt %, less than 0.001 wt %, less than 0.0001 wt %, or less than 0.00001 wt % of FD&C Blue No. 1, FD&C Blue No. 2, FD&C Green No. 3, FD&C Yellow No. 5 (tartrazine), FD&C Yellow No. 6, FD&C Red No. 3, or FD&C Red No. 40, or the lake pigments of any of these, or any combinations thereof. In certain embodiments, one or more of the coating layers, including one or more of the nutrient layers, of the beadlets comprise one or more natural colorants.

In one embodiment, the plurality of beadlets comprise a solid core comprising MCC; an initial nutrient layer surrounding the core, comprising at least one nutrient and one or more excipients; an additional nutrient layer surrounding the first nutrient layer, comprising at least one nutrient; and an outer coating layer that comprises corn zein. There may be one or more other nutrient layers located between the initial nutrient layer and the additional nutrient layer.

In some embodiments, the solid beadlets comprising a core and one or more coatings have an average diameter of between about 0.5 mm to about 10 mm, about 0.5 mm to about 8 mm, about 0.5 mm to about 6 mm, about 0.5 mm to about 4 mm, about 0.5 mm to about 2.5 mm, or about 1 mm to about 2 mm.

In some embodiments, the beadlets begin to dissolve within 15 minutes, within 10 minutes, within 5 minutes, within 1 minute, or within 30 seconds of contact with an aqueous solution.

III. Mini-Tab

Provided herein are dietary supplement compositions comprising a plurality of solid mini-tabs comprising at least one nutrient miscible in an aqueous solution. In some embodiments, nutrients miscible in aqueous solution include those that are soluble in aqueous solution, will suspend in aqueous solution, or will dissolve in aqueous solution as a salt, or any combinations thereof. In some embodiments, the mini-tabs comprise at least one nutrient soluble in an aqueous solution. In certain embodiments, the mini-tabs comprise one or more nutrients that are soluble in the gastrointestinal tract of a mammal. The mini-tabs may comprise one or more nutrients that are soluble in the small intestine of a mammal, the large intestine of a mammal, or both. In some embodiments, the mini-tabs comprise one or more nutrients that are soluble in the small intestine of a mammal. In some embodiments, the mammal is a human. The one or more nutrients may be, for example, vitamins or dietary minerals, or combinations thereof.

The plurality of solid mini-tabs may comprise one or more excipients, for example one or more binders, fillers, diluents, lubricants, or any combination thereof. In certain embodiments, the excipient is selected from the group consisting of cellulosic material, citric acid, starch, protein, alginate, calcium phosphate salts (such as tricalcium phosphate and dicalcium phosphate), lecithin, and silica. In some embodiments, the cellulosic material is microcrystalline cellulose (MCC). The starch may be corn starch, rice starch, pea starch, tapioca starch, or a combination thereof. In some embodiments, the starch is pregelatinized. In some embodiments, the excipient is a vegetable gum, or mixture of vegetable gums. In certain embodiments, the protein is zein, such as corn zein. The one or more excipients may include one or more excipients combined with a nutrient to form the mini-tabs; or one or more excipients associated with one or more nutrients as a nutrient compound; or any combinations thereof.

In certain embodiments, the mini-tabs comprise one or more layers. For example, the mini-tabs may comprise a solid base form comprising at least one aqueous-miscible nutrient and at least one excipient, and one or more layers surrounding the base form. The one or more layers may comprise one or more excipients. In some embodiments, the min-tabs comprise a layer that consists essentially of an excipient. The layer may comprise up to 95 wt %, up to 98 wt %, up to 99 wt %, up to 99.5 wt %, up to 99.9 wt %, or up to 99.99 wt % of one or more excipients. In one embodiment, the layer comprises zein, such as corn zein.

In some embodiments, the mini-tabs comprise an outermost layer that may help maintain the heterogeneous mixture of the mini-tabs in the oil, and may prevent the nutrients of the mini-tabs from contacting the oil. Separating certain nutrients by using the mini-tabs-in-oil compositions described herein may help maintain the stability and activity of certain nutrients, which in turn may improve absorption and/or activity in the body. For example, iron salt may interact with and negatively impact the potency of vitamin D3, vitamin E, vitamin B12, DHA and EPA. In compositions comprising two or more of these nutrients, locating the iron in the solid mini-tabs and one or more of the other nutrients in the oil may prevent or reduce interactions between iron and the other nutrients.

In certain embodiments, the outer layer comprises a protein, such as corn zein. In some embodiments, the outer layer consists essentially of a protein, such as corn zein. The corn zein may, in some embodiments, be derived from corn that has not been genetically modified.

In certain embodiments, the mini-tabs are essentially free of certain excipients. For example, the mini-tabs may be essentially free of titanium (such as titanium dioxide), polymers synthesized from petroleum or petroleum products, polyvinylpyrrolidine, polyethylene glycols, talc, disaccharides (such as sucrose), or lac resin (shellac), or any combinations thereof. In certain embodiments, the mini-tabs comprise less than 0.1 wt %, less than 0.01 wt %, less than 0.001 wt %, or less than 0.0001 wt % of titanium (such as titanium dioxide), polymers synthesized from petroleum or petroleum products, polyvinylpyrrolidine, polyethylene glycols, talc, disaccharides (such as sucrose), or lac resin (shellac), or any combinations thereof.

In certain embodiments, the mini-tabs are essentially free of artificial colorants. For example, the mini-tabs may be essentially free of FD&C Blue No. 1, FD&C Blue No. 2, FD&C Green No. 3, FD&C Yellow No. 5 (tartrazine), FD&C Yellow No. 6, or FD&C Red No. 3, FD&C Red No. 40, or the lake pigments of any of these, or any combinations thereof. In certain embodiments, the mini-tabs comprise less than 0.1 wt %, less than 0.01 wt %, less than 0.001 wt %, less than 0.0001 wt %, or less than 0.00001 wt % of FD&C Blue No. 1, FD&C Blue No. 2, FD&C Green No. 3, FD&C Yellow No. 5 (tartrazine), FD&C Yellow No. 6, FD&C Red No. 3, or FD&C Red No. 40, or the lake pigments of any of these, or any combinations thereof. In certain embodiments, the mini-tabs, such as one or more layers is present, comprise one or more natural colorants.

In one embodiment, the plurality of mini-tabs comprise a solid base form comprising at least one nutrient and one or more excipients; and an outer coating layer that comprises corn zein. In some embodiments, the solid base form comprises a plurality of nutrients.

In some embodiments, the mini-tabs have an average diameter of between about 0.5 mm to about 10 mm, about 0.5 mm to about 8 mm, about 0.5 mm to about 6 mm, about 0.5 mm to about 4 mm, about 0.5 mm to about 2.5 mm, or about 1 mm to about 2 mm.

In some embodiments, the mini-tabs begin to dissolve within 15 minutes, within 10 minutes, within 5 minutes, within 1 minute, or within 30 seconds of contact with an aqueous solution.

The mini-tabs may be generally spherical in shape, or generally ovoid in shape, or generally cylindrical with hemispherical ends, or may have one or more flat surfaces, or may be generally disk-shaped. The mini-tabs comprise a solid material, for example by compressing a mixture of one or more nutrients and one or more excipients to produce solid base forms. In certain embodiments, one or more coating layers may then be applied to the solid base forms to produce the mini-tabs. In some embodiments, the mini-tabs are essentially free of disaccharides, essentially free of monosaccharides, or essentially free of both disaccharides and monosaccharides. In some embodiments, the mini-tabs are essentially free of glucose, fructose, galactose, mannose, arabinose, erythrose, and allose. In other embodiments, the mini-tabs are essentially free of sucrose, lactose, lactulose, and maltose. In certain embodiments, the mini-tabs are essentially free of glucose, fructose, galactose, mannose, arabinose, erythrose, allose, sucrose, lactose, lactulose, and maltose. In one embodiment, the mini-tabs are essentially free of sucrose.

IV. Aqueous-Miscible Nutrients

As described above, the beadlets or mini-tabs comprise at least one nutrient miscible in an aqueous solution. The at least one nutrient may be, for example, a vitamin, probiotic, or dietary mineral. In some embodiments, the nutrient is selected from the group consisting of B vitamins, boron, magnesium, zinc, probiotics, choline, iodine, chromium, selenium, Vitamin C, and iron. In some embodiments, the nutrient is selected from the group consisting of B vitamins, boron, magnesium, calcium, and iron.

In some embodiments, the beadlets comprise one or more B vitamins. In some embodiments, the mini-tabs comprise one or more B vitamins. For example, the beadlets or mini-tabs may comprise vitamin B1, vitamin B6, vitamin B3, vitamin B12, folate, or a combination thereof. In some embodiments, the vitamin B3 is nicotinamide riboside. The vitamin B6 may be present in any suitable form, for example as a vitamin B6 compound. In some variations, the vitamin B3 is present as pyridoxal-5'-phosphate, a pyridoxal-5'-phosphate salt, pyridoxine hydrochloride, or any combinations thereof. In one embodiment, the beadlets or mini-tabs comprise vitamin B12. The vitamin B12 may be, for example, methylcobalamin. In some embodiments, the beadlets or mini-tabs comprise folate. The folate may be, for example, a (6S)-5-methyltetrahydrofolate (5MTHF) salt. In one embodiment, the beadlets or mini-tabs comprise 5MTHF glucosamine salt. In some variations, the folate is not folic acid. Providing folate as a 5MTHF salt rather than folic acid may reduce accumulation of unmetabolized folic acid in the body. Accumulation of unmetabolized folic acid can have negative effects on the activity of enzymes that utilize folate. In some embodiments, the beadlets or mini-tabs comprise both folate and vitamin B12. Deficiency in vitamin B12 can sometimes be masked by the intake of folate, wherein an individual does not notice or have the side effects of a vitamin B12 deficiency but can still be deficient, and sustain physiological damage from said deficiency. Including vitamin B12 and folate may be important to maintaining adequate levels of both vitamins, and avoiding the detrimental effects of vitamin B12 deficiency. In some embodiments, the beadlets or mini-tabs comprise vitamin B1, in other embodiments, the beadlets or mini-tabs comprise vitamin B6. In still further embodiments, the beadlets or mini-tabs comprise vitamin B3. In certain embodiments, the beadlets or mini-tabs comprise vitamin B12 and folate. In other embodiments, the beadlets or mini-tabs comprise vitamin B1, vitamin B6, and vitamin B3.

In some embodiments, the beadlets comprise boron. In some embodiments, the mini-tabs comprise boron. The boron may be present in any suitable form, for example as a boron compound. In certain embodiments, the beadlets or mini-tabs comprise a carbohydrate-boron complex. This may include complexes of boron with one or more sugar and/or sugar alcohol molecules. The sugar molecule may be a monosaccharide, disaccharide, trisaccharide, oligosaccharide, or polysaccharide, and the sugar alcohol may be any alcohols of any of those. Suitable sugars and sugar alcohols may include those with three to six carbons, for example pentoses or hexoses. The carbohydrate-boron complex may include complexes between boron and fructose, glucose, mannose, sorbose, sorbulose, sorbitol, xylose, xylulose, or xylitol. For example, the boron carbohydrate-boron complex may be fructoborate, or borogluconate In some embodiments, the boron is in the form of a salt of a carbohydrate-boron complex, for example a calcium, magnesium, manganese, iron, copper, zinc, chromium, or vanadium salt. In certain embodiments, the boron is in the form of a fructoborate salt. In one embodiment, the beadlets or mini-tabs comprise calcium fructoborate. In other embodiments, the boron is in the form of a borogluconate salt, such as calcium borogluconate. In certain embodiments, the boron is not boric acid, sodium borate, or boric anhydride.

In some embodiments, the beadlets comprise magnesium. In some embodiments, the mini-tabs comprise magnesium. The magnesium may be present in any suitable form, for example as a magnesium compound. In some variations, the magnesium is in the form of a magnesium salt. Magnesium salts may include magnesium ascorbate, magnesium aspartate, magnesium citrate, magnesium gluconate, magnesium glycerophosphate, magnesium glycinate, magnesium lactate, magnesium levulinate, magnesium malate, magnesium orotate, magnesium pidolate, and magnesium taurate. In some variations, the magnesium is magnesium malate, for example dimagnesium malate. In certain variations, the magnesium is in the form of magnesium oxide. In one embodiment, the beadlets or mini-tabs comprise magnesium oxide encapsulated within a phospholipid membrane. For example, in one embodiment, the beadlets or mini-tabs comprise a magnesium-sucrosome compound, wherein magnesium oxide is encapsulated within a sucrosome particle, or a plurality of sucrosome particles. The sucrosome particle may comprise sucrose esters of fatty acids. The magnesium, such as magnesium oxide, may be encapsulated within the particle, or plurality of particles. In some embodiments, the sucrosome particle further comprises a calcium phosphate, such as tricalcium phosphate. In certain embodiments, the sucrosome particle further comprises lecithin. The use of sucrosome particles to encapsulate magnesium may improve absorption of the magnesium by the digestive system (e.g., the small intestine) compared to magnesium which is not encapsulated. One example of such an encapsulated magnesium compound is Sucrosomial® magnesium. In another embodiment, the magnesium is in the form of dimagnesium malate.

In some embodiments, the beadlets comprise iron. In some embodiments, the mini-tabs comprise iron. The iron may be present in any suitable form, for example as an iron compound. In some embodiments, the iron is in the form of an iron salt. Iron salts may include salts of iron and amino acids or organic acids. Iron salts may include ferrous bisglycinate, ferric bisglycinate, ferrous fumarate, ferrous gluconate, ferrous lactate, or ferrous succinate. For example, in one embodiment, the beadlets or mini-tabs comprise ferrous bisglycinate. The use of ferrous bisglycinate may increase absorption of iron by the digestive system (e.g., the small intestine), reduce nausea associated with consuming iron, or both, as compared to other forms of iron. In some embodiments, the iron is present as an iron-sucrosome compound, wherein the iron is encapsulated within a sucrosome particle, or plurality of sucrosome particles, as described above. In some embodiments, the encapsulated iron is an iron salt.

In some embodiments, the beadlets comprise zinc. In some embodiments, the mini-tabs comprise zinc. The zinc may be present in any suitable form, for example a zinc compound. In some embodiments, the zinc is in the form of a zinc salt. Zinc salts may include zinc acetate, zinc ascorbate, zinc carnosinate, zinc citrate, zinc glycerophosphate, zinc glycinate, zinc lactate, zinc mono-L-methionate, and zinc succinate. In one embodiment, the zinc is in the form of zinc bisglycinate.

In some embodiments, the beadlets comprise calcium. In some embodiments, the mini-tabs comprise calcium. The calcium may be present in any suitable form, for example as a calcium chelate or calcium salt. Calcium salts may include calcium acetate, calcium ascorbate, calcium citrate, calcium glycerophosphate, calcium glycinate, calcium lactate, calcium malate, and calcium citrate-malate. In some embodiments, the calcium is in the form of a calcareous marine algae extract. In one embodiment, the calcium is in the form of Lithothamnium spp. calcareous marine algae. In other embodiments, the calcium is in the form of a calcium-sucrosome compound. In some embodiments, the calcium is calcium bisglycinate.

In some embodiments, the beadlets comprise one or more probiotics. In some embodiments, the mini-tabs comprise one or more probiotics. The one or more probiotics may comprise one or more spore-forming species, one or more non-spore-forming species, or any combinations thereof. In one embodiment, the one or more probiotics are spore-forming species. In another embodiment, the one or more probiotics are non-spore-forming species. In certain embodiments, the one or more probiotics comprise one or more *Bacillus* species, or one or more *Bacillus* strains, or a combination thereof. In other embodiments, the one or more probiotics comprise one or more *Bifidobacterium* species, or one or more *Bifidobacterium* strains, or a combination thereof. In certain embodiments, the one or more probiotics comprise one or more *Lactobacillus* species, one or more *Lactobacillus* strains, or a combination thereof. In certain embodiments, one or more probiotics comprise one or more cocci species, one or more cocci strains, or a combination thereof.

In some embodiments, the beadlets comprise choline. In some embodiments, the mini-tabs comprise choline. The choline may be from any suitable source. In some embodiments, the choline is derived from a natural source.

In some embodiments, the beadlets comprise iodine. In some embodiments, the mini-tabs comprise iodine. The iodine may be present in any suitable form, for example as an iodine compound. In some embodiments, the iodine is an iodine salt, for example potassium iodide. In certain embodiments, the iodine, such potassium iodide, is derived from kelp.

In some embodiments, the beadlets comprise selenium. In some embodiments, the mini-tabs comprise selenium. The selenium may be present in any suitable form, for example as a selenium compound. In some embodiments, the selenium is in the form of L-selenocysteine or L-selenomethionine.

In some embodiments, the beadlets comprise chromium. In some embodiments, the mini-tabs comprise chromium. The chromium may be present in any suitable form, for example as a chromium compound. In some embodiments, the chromium is in the form of a compound comprising $Cr^t$. For example, chromium may be present in the form of dinicocysteinate, nicotinate, or picolinate.

In some embodiments the beadlets comprise Vitamin C. In some embodiments the mini-tabs comprise Vitamin C. The vitamin C may be from any suitable source. In some embodiments, the vitamin C is derived from a natural source, for example from citrus fruit, tomatoes, red peppers or potatoes. The vitamin C may be in any suitable form, for example as ascorbic acid, an ascorbate salt, or an ascorbate chelate.

The beadlets may comprise at least one, at least two, at least three, at least four, at least five, at least six, at least seven, or at least eight nutrients selected from the group consisting of B vitamins, boron, magnesium, iron, zinc, iodine, selenium, choline, chromium, probiotics, and vitamin C. In some embodiments, the beadlets comprise at least one, at least two, at least three, at least four, or at least five nutrients selected from the group consisting of B vitamins, boron, magnesium, and iron. The B vitamins may be, for example, vitamin B1, vitamin B6, vitamin B3, vitamin B12, or folate, or a combination thereof. In some embodiments, the B vitamins are vitamin B12 or folate, or a combination thereof. In some variations, the beadlets comprise vitamin B12, folate, boron, magnesium and iron. In other variations, the beadlets comprise vitamin B1, vitamin B6, vitamin B3, boron, magnesium, zinc, selenium, and chromium.

The mini-tabs may comprise at least one, at least two, at least three, at least four, at least five, at least six, at least seven, or at least eight nutrients selected from the group consisting of B vitamins, boron, magnesium, iron, zinc, iodine, selenium, choline, chromium, probiotics, and vitamin C. In some embodiments, the mini-tabs comprise at least one, at least two, at least three, at least four, or at least five nutrients selected from the group consisting of B vitamins, boron, magnesium, and iron. The B vitamins may be, for example, vitamin B1, vitamin B6, vitamin B3, vitamin B12, or folate, or a combination thereof. In some embodiments, the B vitamins are vitamin B12 or folate, or a combination thereof. In some variations, the mini-tabs comprise vitamin B12, folate, boron, magnesium and iron. In other variations, the mini-tabs comprise vitamin B1, vitamin B6, vitamin B3, boron, magnesium, zinc, selenium, and chromium. In certain embodiments, the mini-tabs comprise one or more probiotics.

V. Oil

The dietary supplement compositions provided herein also comprise oil. In certain embodiments, the oil is liquid, and comprises one or more nutrients that are fat-soluble. A fat-soluble nutrient may be a vitamin, dietary mineral, or fatty acid. For example, the fat-soluble nutrient may be selected from the group consisting of vitamin K, vitamin D, vitamin E, mixed carotenoids, Medium Chain Triglycerides (MCTs), one or more probiotics, and omega-3 fatty acids. In certain embodiments, the oil is liquid above about −40° F., above about −30° F., above about −20° F., above about −10° F., above about 0° F., above about 10° F., above about 20° F., above about 30° F., above about 40° F., above about 50° F., above about 60° F., above about 70° F., above about 80° F., or above about 90° F. In some embodiments, the oil is liquid above about −40° F., or above about −30° F.

It should be understood that the oil may be one oil, or a mixture of oils. In certain variations, the oil comprises one or more fat-soluble nutrients, wherein at least one fat-soluble nutrient is itself an oil.

A. Nutrients

In some embodiments, the oil comprises one or more omega-3 fatty acids. For example, in certain embodiments, the oil comprises docosahexaenoic acid (DHA), eicosapentaenoic acid (EPA), or a combination thereof. In some variations, the oil comprises algal oil, wherein the algal oil comprises DHA, EPA, or a combination thereof. The algal oil may be derived from one or more species of algae, for example one or more species Schizochytrium. In other embodiments, the oil comprises DHA, EPA, or a combination thereof, wherein the DHA, EPA, or combination thereof is derived from algal oil. The DHA, EPA, or combination thereof may be derived from one or more species of algae, for example one or more species of Schizochytrium. In certain embodiments, the omega-3 fatty acids, such as DHA, EPA, or combinations thereof, are derived from vegan sources, such as algae. In certain embodiments, the algal oil comprises up to about 10 wt %, up to about 20 wt %, up to about 30 wt %, up to about 40 wt %, up to about 50 wt %, up to about 60 wt %, up to about 70 wt %, up to about 80 wt %, up to about 90 wt %, or up to about 99 wt % omega-3 fatty acids. The omega-3 fatty acids may be, for example, DHA and EPA.

In some embodiments, the oil comprises vitamin D. The vitamin D may be vitamin D3 (cholecalciferol). In some variations, the vitamin D is derived from a non-animal source, such as lichen.

In certain embodiments, the oil comprises vitamin K. The vitamin K may be vitamin K2. In some embodiments, the vitamin K2 is MK-7. In certain embodiments, the vitamin K, such as MK-7, is from a non-soy source. In some embodiments, the vitamin K, such as MK-7, is bioidentical, for example synthetically produced but identical chemically to MK-7 obtained from natural sources, such as from a non-soy source. Vitamin K2 may support the function of calcium-binding proteins, and/or maintain calcium levels in certain tissues.

In certain embodiments, the oil comprises vitamin E. The vitamin E may comprise tocopherols, tocotrienols, or any combinations thereof. In some embodiments, the vitamin E is a mixture of tocopherols. In some embodiments, the oil comprises at least two compounds selected from the group consisting of α-tocopherol, β-tocopherol, γ-tocopherol, δ-tocopherol, α-tocotrienol, β-tocotrienol, γ-tocotrienol, δ-tocotrienol. In some embodiments, the oil comprises at least two compounds selected from the group consisting of α-tocopherol, β-tocopherol, γ-tocopherol, and δ-tocopherol. Thus, the oil may comprise vitamin E, wherein the vitamin E is at least two, at least three, or at least four compounds selected from the group consisting of α-tocopherol, β-tocopherol, γ-tocopherol, and δ-tocopherol. In some embodiments, the oil comprises less than 1 wt %, less than 0.5 wt %, less than 0.1 wt %, or less than 0.01 wt % of one or more tocopherol esters. In some embodiments, the vitamin E comprises α-tocopherol, and one or more other tocopherols or tocotrienols. In certain embodiments, the vitamin E comprises a mixture of tocopherols, and is essentially free of tocotrienols, for example comprising less than 1 wt %, less than 0.5 wt %, less than 0.1 wt %, or less than 0.01 wt % of one or more tocotrienols. In some embodiments, the vitamin E comprises α-tocopherol and γ-tocopherol in a ratio of about 0.7:1 to 1:0.7 alpha:gamma, for example about 0.8:1 to about 1:0.8, about 0.9:1 to about 1:0.9, or about 1:1.

In some embodiments, the oil comprises one or more carotenoids. The one or more carotenoids may be, for example, alpha-carotene, beta-carotene, cryptoxanthin, lutein, or lycopene, or any combinations thereof. The one or more carotenoids may be from natural sources, for example derived from *Dunaliella* algae, carrot oil, palm oil, tomato, marigold, red palm oil, or any combinations thereof. Certain carotenoids, such as beta-carotene, alpha-carotene, or cryptoxanthin, may be forms of provitamin A, which may have some vitamin A activity and may in some embodiments be converted to vitamin A after ingestion by a subject.

In other embodiments, the oil comprises Medium Chain Triglycerides (MCTs). The MCTs may be from any suitable source, and may include, for example, triglycerides with aliphatic tails comprising eight, ten, or twelve carbons. In some embodiments, the MCTs are derived from a natural source, such as coconut oil. In certain embodiments, the oil comprises coconut oil.

In some embodiments, the oil comprises one or more probiotics. The one or more probiotics may comprise one or more spore-forming species, one or more non-spore-forming species, or any combinations thereof. In one embodiment, the one or more probiotics are spore-forming species. In another embodiment, the one or more probiotics are non-spore-forming species. In certain embodiments, the one or more probiotics comprise one or more *Bacillus* species, or one or more *Bacillus* strains, or a combination thereof. In other embodiments, the one or more probiotics comprise one or more *Bifidobacterium* species, or one or more *Bifidobacterium* strains, or a combination thereof. In certain embodiments, the one or more probiotics comprise one or more *Lactobacillus* species, one or more *Lactobacillus* strains, or a combination thereof. In certain embodiments, one or more probiotics comprise one or more cocci species, one or more cocci strains, or a combination thereof.

The oil may comprise at least one nutrient, at least two nutrients, at least three nutrients, at least four nutrients, at least five nutrients, at least six nutrients, at least seven nutrients, or more selected from the group consisting of vitamin K, vitamin D, vitamin E, omega-3 fatty acids, one or more carotenoids, MCTs, one or more probiotics. The oil may comprise at least one nutrient, at least two nutrients, at least three nutrients, or at least four nutrients selected from the group consisting of vitamin K, vitamin D, vitamin E, and omega-3 fatty acids. In some variations, the oil comprises vitamin K, vitamin D, vitamin E, and omega-3 fatty acids. In certain embodiments, the oil comprises vitamin K as vitamin K2; vitamin D as vitamin D3; vitamin E as two or more tocopherols; and one or more omega-3 fatty acids.

In some embodiments, the oil is translucent. In other embodiments, the oil is transparent.

B. Other Components

The oil may comprise one or more excipients, for example one or more binders, fillers, diluents, lubricants, or viscosity adjusters, or any combinations thereof. In some variations, the one or more excipients are selected from the group consisting of ascorbyl palmitate, plant oils, silica, medium chain triglycerides. Plant oils may be coconut oil or sunflower oil.

The oil may further comprise one or more flavor agents or odorant agents, or any combinations thereof. A flavor agent may comprise one or more compounds that impart a flavor to the dietary supplement composition. An odorant agent comprises one or more compounds that impart an odor to the dietary supplement composition. In some embodiments, a flavor agent may also act as an odor agent. Including one or more flavor agents and/or odorant agents in the oil may increase compliance with a dosing regimen. For example, in certain embodiments, the oil comprises algal oil, which may impart an undesirable odor (e.g., similar to fish). Including one or more flavor agents and/or odorant agents in an oil that also comprises algal oil may decrease the perception of an undesirable "fishy" odor, which may in turn increase compliance with the dosing regimen of the dietary supplement composition.

The flavor agent or odorant agent may be derived from natural sources. In some embodiments, the odorant agent is a plant oil, a compound derived from plants, or an oil comprising one or more compounds derived from a plant. In some embodiments, the flavor agent is a plant oil, a compound derived from plants, or an oil comprising one or more compounds derived from a plant. For example, in certain embodiments, the flavor agent or odorant agent comprises a flavor, oil, extract, or scent selected from the group consisting of mint, vanilla, ginger, grapefruit, rosemary, lemon, lime, and orange. For example, the flavor agent or odorant agent may be vanilla flavor, mint flavor, mint oil, ginger flavor, ginger oil, grapefruit flavor, grapefruit oil, rosemary flavor, rosemary oil, lemon flavor, lemon oil, orange flavor, or orange oil. In one embodiment, the flavor agent or odorant agent comprises a mint oil. In one example, the mint oil is peppermint oil. In another embodiment, the flavor agent or odorant agent comprises vanilla flavor. In one embodiment, the vanilla flavor is derived from natural sources.

VI. Nutrient Content

The dietary supplement compositions described herein comprise at least two nutrients as described above. In some embodiments, the nutrients are independently selected from the group consisting of dietary minerals, vitamins, probiotics, and fatty acids. The compositions may comprise any suitable amount of the two or more nutrients.

In certain embodiments, the dietary supplement composition comprises between about 45 micrograms (mcg) to about 135 mcg, between about 67.5 mcg to about 126 mcg, between about 67.5 mcg to about 120 mcg, between about 67.5 mcg to about 112.5 mcg, between about 80 mcg to about 100 mcg, between about 81 mcg to about 120 mcg, between about 81 mcg to about 112.5 mcg, between about 81 mcg to about 99 mcg, or about 90 mcg vitamin K. In some embodiments, the dietary supplement composition comprises between about 81 mcg to about 120 mcg vitamin K. In some embodiments, the composition comprises between about 80 mcg to about 100 mcg vitamin K. In some embodiments, the composition comprises between about 81 mcg to about 112.5 mcg vitamin K. In certain embodiments, the composition comprises between about 81 mcg to about 99 mcg vitamin K. In one variation, the composition comprises about 90 mcg vitamin K. In some embodiments, the vitamin K is vitamin K2. In one embodiment, the vitamin K is MK7.

In certain embodiments, the dietary supplement composition comprises between about 1000 IU to about 3000 IU, between about 1500 IU to about 2800 IU, between about 1500 IU to about 2660 IU, between about 1500 IU to about 2500 IU, between about 1800 IU to about 3000 IU, between about 1800 IU to about 2660 IU, between about 1800 IU to about 2500 IU, between about 1800 IU to about 2200 IU, or about 2000 IU of vitamin D. In some embodiments, the composition comprises between about 1800 IU to about 2660 IU vitamin D. In other embodiments, the composition comprises between about 1800 IU to about 2500 IU vitamin D. In still other embodiments, the composition comprises between about 1800 IU to about 2200 IU vitamin D. In one embodiment, the composition comprises about 2000 IU vitamin D. In some embodiments, the vitamin D is vitamin D3 (cholecalciferol).

In certain embodiments, the dietary supplement composition comprises between about 4 mcg to about 24 mcg, between about 6 mcg to about 24 mcg, between about 10 mcg to about 24 mcg, between about 4 mcg to about 20 mcg, between about 6 mcg to about 20 mcg, between about 10 mcg to about 20 mcg, between about 4 mcg to about 16 mcg, between about 6 mcg to about 16 mcg, between about 10 mcg to about 16 mcg, between about 14 mcg to about 18 mcg, between about 15 mcg to about 17 mcg, 4 mcg to about 12 mcg, between about 6 mcg to about 12 mcg, between about 6 mcg to about 11.2 mcg, between about 6 mcg to about 10.64 mcg, between about 6 mcg to about 10 mcg, between about 7 mcg to about 9 mcg, between about 7.2 mcg to about 11.2 mcg, between about 7.2 mcg to about 10.64 mcg, between about 7.2 mcg to about 10 mcg, between about 7.2 mcg to about 8.8 mcg, or about 8 mcg, or about 16 mcg vitamin B12. In some embodiments, the composition comprises between about 7 mcg to about 9 mcg vitamin B12. In other embodiments, the composition comprises between about 7.2 mcg to about 10.64 mcg vitamin B12. In other embodiments, the composition comprises between about 7.2 mcg to about 10 mcg vitamin B12. In still other embodiments, the composition comprises between about 7.2 mcg to about 8.8 mcg vitamin B12. In other embodiments, the composition comprises between about 14.4 mcg to about 24 mcg vitamin B12. In further embodiments, the composition comprises between about 14.4 mcg to about 21 mcg vitamin B12. In certain embodiments, the composition comprises between about 14.4 mcg to about 20 mcg vitamin B12. In still other embodiments, the composition comprises between about 14.4 mcg to about 17.6 mcg vitamin B12. In one embodiment, the composition comprises about 8 mcg vitamin B12. In another embodiment, the composition comprises about 16 mcg vitamin B12. In one embodiment, the vitamin B12 is methylcobalamin.

In certain embodiments, the dietary supplement composition comprises between about 0.5 mg to about 1.5 mg, between about 0.75 mg to about 1.4 mg, between about 0.75 mg to about 1.33 mg, between about 0.75 mg to about 1.25 mg, between about 0.9 mg to about 1.33 mg, between about 0.9 mg to about 1.25 mg, between about 0.9 mg to about 1.1 mg, or about 1.0 mg boron. In some embodiments, the composition comprises between about 0.9 mg to about 1.33 mg boron. In other embodiments, the composition comprises between about 0.9 mg to about 1.25 mg boron. In still other embodiments, the composition comprises between about 0.9 mg to about 1.1 mg boron. In one embodiment, the composition comprises about 1.0 mg boron. In some embodiments, the boron is in the form of a carbohydrate-boron complex. In certain embodiment, the boron is in the form of a fructoborate salt. In one embodiment, the boron is in the form of calcium fructoborate. It should be understood that if the composition comprises, for example, 1.0 mg of boron, and the boron is present in the form of a chemical compound comprising boron, the composition may comprise greater than 1.0 mg of the boron compound such that the total boron content of the composition is 1.0 mg.

In certain embodiments, the dietary supplement composition comprises between about 5 IU to about 15 IU, between about 7.5 IU to about 14 IU, between about 7.5 IU to about 13.3 IU, between about 7.5 IU to about 12.5 IU, between about 9 IU to about 13.3 IU, between about 9 IU to about 12.5 IU, between about 9 IU to about 11 IU, or about 10 IU of vitamin E. In some embodiments, the composition comprises between about 9 IU to about 13.3 IU vitamin E. In other embodiments, the composition comprises between about 9 IU to about 12.5 IU vitamin E. In still other embodiments, the composition comprises between about 9 IU to about 11 IU vitamin E. In one embodiment, the composition comprises about 10 IU vitamin E. In some embodiments, the vitamin E is a mixture of tocopherols. In certain embodiments, the IU value of vitamin E is based on the content of α-tocopherol, and not on any other forms of vitamin E which may be present.

In certain embodiments, the dietary supplement composition comprises between about 25 mg to about 75 mg, between about 37.5 mg to about 70 mg, between about 37.5 mg to about 66.5 mg, between about 37.5 mg to about 62.5 mg, between about 45 mg to about 66.5 mg, between about 45 mg to about 62.5 mg, between about 45 mg to about 55 mg, about 50 mg, between about 17.5 mg to about 52.5 mg, between about 31.5 mg to about 49 mg, between about 31.5 mg to about 46 mg, between about 31.5 mg to about 43.8 mg, between about 31.5 mg to about 38.5 mg, between about 34 mg to about 41.8 mg, between about 34 mg to about 42.5 mg, between about 34 mg to about 49 mg, or about 35 mg, or about 38 mg magnesium. In some embodiments, the composition comprises between about 31.5 mg to about 43.8 mg. In some embodiments, the composition comprises between about 45 mg to about 66.5 mg magnesium. In other embodiments, the composition comprises between about 45 mg to about 62.5 mg magnesium. In still other embodiments, the composition comprises between about 45 mg to about 55 mg magnesium. In one embodiment, the composition comprises about 50 mg magnesium. In still further embodiments, the composition comprises about 38 mg magnesium, or about 35 mg magnesium. In some embodiments, the magnesium is in the form of a magnesium salt. In other embodiments, the magnesium is in the form of a magnesium-sucrosome compound. In some embodiments, the magnesium is dimagnesium malate. It should be understood that if the composition comprises, for example, 50 mg of magnesium, and the magnesium is present in the form of a chemical compound comprising magnesium, the composition may comprise greater than 50 mg of the magnesium compound such that the total magnesium content of the composition is 50 mg.

In certain embodiments, the dietary supplement composition comprises between about 4 mg to about 27 mg, between about 6 mg to about 27 mg, between about 8 mg to about 27 mg, between about 10 mg to about 27 mg, between about 12 mg to about 27 mg, between about 14 mg to about 27 mg, about 4 mg to about 24 mg, between about 6 mg to about 24 mg, between about 8 mg to about 24 mg, between about 10 mg to about 24 mg, between about 12 mg to about 24 mg, between about 14 mg to about 24 mg, between about 16 mg to about 24 mg, between about 18 mg to about 24 mg, between about 4 mg to about 22 mg, between about 6 mg to about 22 mg, between about 8 mg to about 22 mg, between about 10 mg to about 22 mg, between about 12 mg to about 22 mg, between about 14 mg to about 22 mg, between about 16 mg to about 22 mg, between about 4 mg to about 20 mg, between about 6 mg to about 20 mg, between about 8 mg to about 20 mg, between about 10 mg to about 20 mg, between about 12 mg to about 20 mg, between about 14 mg to about 20 mg, between about 16 mg to about 20 mg, between about 4 mg to about 12 mg, between about 6 mg to about 11.2 mg, between about 6 mg to about 10.64 mg, between about 6 mg to about 10 mg, between about 7.2 mg to about 10.64 mg, between about 7.2 mg to about 10 mg, between about 7.2 mg to about 8.8 mg, between about 7 mg to about 9 mg, or about 8 mg, or about 18 mg iron. In some embodiments, the composition comprises between about 7 mg to about 9 mg iron. In certain embodiments, the composition comprises between about 7.2 mg to about 10.64 mg iron. In other embodiments, the composition comprises between about 7.2 mg to about 10 mg iron. In still other embodiments, the composition comprises between about 7.2 mg to about 8.8 mg iron. In one embodiment, the composition comprises about 8 mg iron. In other embodiments, the composition comprises between about 16 mg to about 27 mg iron. In other embodiments, the composition comprises between about 16 mg to about 23 mg iron. In still other embodiments, the composition comprises between about 16 mg to about 22 mg iron. In other embodiments, the composition comprises between about 16 mg to about 20 mg iron. In one embodiment, the composition comprises about 18 mg iron. In certain embodiments, the iron is present in the form of an iron salt. In other embodiments, the iron is in the form of ferrous bisglycinate. It should be understood that if the composition comprises, for example, 8 mg of iron, and the iron is present in the form of a chemical compound comprising iron, the composition may comprise greater than 8 mg of the iron compound such that the total iron content of the composition is 8 mg.

In certain embodiments, the dietary supplement composition comprises between about 25 mg to about 75 mg, between about 37.5 mg to about 70 mg, between about 37.5 mg to about 66.5 mg, between about 37.5 mg to about 62.5 mg, between about 45 mg to about 66.5 mg, between about 45 mg to about 62.5 mg, between about 45 mg to about 55 mg, or about 50 mg calcium. In some embodiments, the composition comprises between about 45 mg to about 66.5 mg calcium. In other embodiments, the composition comprises between about 45 mg to about 62.5 mg calcium. In still other embodiments, the composition comprises between about 45 mg to about 55 mg calcium. In one embodiment, the composition comprises about 50 mg calcium. In some embodiments, the calcium is in the form of a Lithothamnium spp. calcareous marine algae. In other embodiments, the calcium is in the form of a calcium-sucrosome compound. In some embodiments, the calcium is calcium bisglycinate. It should be understood that if the composition comprises, for example, 50 mg of calcium, and the calcium is present in the form of a chemical compound comprising calcium, the composition may comprise greater than 50 mg of the calcium compound such that the total calcium content of the composition is 50 mg.

In certain embodiments, the dietary supplement composition comprises between about 300 mcg to about 3000 mcg, between about 450 mcg to about 3000 mcg, between about 540 mcg to about 3000 mcg, between about 700 mcg to about 3000 mcg, between about 1000 mcg to about 3000 mcg, between about 1300 mcg to about 3000 mcg, between about 1600 mcg to about 2600 mcg, between about 1600 mcg to about 2600 mcg, between about 300 mcg to about 2600 mcg, between about 450 mcg to about 2600 mcg, between about 540 mcg to about 2600 mcg, between about 700 mcg to about 2600 mcg, between about 1000 mcg to about 2600 mcg, between about 1300 mcg to about 2600 mcg, between about 1600 mcg to about 2600 mcg, between about 1600 mcg to about 2600 mcg, between about 300 mcg to about 2500 mcg, between about 450 mcg to about 2500 mcg, between about 540 mcg to about 2500 mcg, between about 700 mcg to about 2500 mcg, between about 1000 mcg to about 2500 mcg, between about 1300 mcg to about 2500 mcg, between about 1600 mcg to about 2500 mcg, between about 1600 mcg to about 2500 mcg, between about 300 mcg to about 2200 mcg, between about 450 mcg to about 2200 mcg, between about 540 mcg to about 2200 mcg, between about 700 mcg to about 2200 mcg, between about 1000 mcg to about 2200 mcg, between about 1300 mcg to about 2200 mcg, between about 1600 mcg to about 2200 mcg, between about 1600 mcg to about 2200 mcg, between about 300 mcg to about 900 mcg, between about 450 mcg to about 840 mcg, between about 450 mcg to about 800 mcg, between about 450 mcg to about 750 mcg, between about 540 mcg to about 800 mcg, between about 540 mcg to about 750 mcg, between about 540 mcg to about 660 mcg, or about 600 mcg, or about 2000 mcg folate. In some embodiments, the composition comprises between about 540 mcg to about 800 mcg folate. In other embodiments, the composition comprises between about 540 mcg to about 750 mcg folate. In still other embodiments, the composition comprises between about 540 mcg to about 660 mcg folate. In one embodiment, the composition comprises about 600 mcg folate. In other embodiments, the composition comprises between about 1800 mcg to about 3000 mcg folate. In another embodiment, the composition comprises between about 1800 mcg to about 2600 mcg folate. In still further embodiments, the composition comprises between about 1800 mcg to about 2500 mcg folate. In other embodiments, the composition comprises between about 1800 mcg to about 2200 mcg folate. In one embodiment, the composition comprises about 2000 mcg folate. In certain embodiments, the folate is in the form of a 5MTHF salt. In one embodiment, the folate is in the form of 5MTHF glucosamine salt. It should be understood that if the composition comprises, for example, 600 mcg of folate, and the folate is present in the form of a chemical compound comprising folate, the composition may comprise greater than 600 mcg of the folate compound such that the total folate content of the composition is 600 mcg.

In certain embodiments, the dietary supplement composition comprises one or more omega-3 fatty acids, wherein the total omega-3 fatty acid content is between about 160 mg to about 480 mg, between about 240 mg to about 450 mg, between about 240 mg to about 425 mg, between about 240 mg to about 400 mg, between about 290 mg to about 425 mg, between about 290 mg to about 400 mg, between about 290 mg to about 350 mg, or about 320 mg. In some embodiments, the composition comprises between about 290 mg to about 425 mg of omega-3 fatty acids. In other embodiments, the composition comprises between about 290 mg to about 400 mg of omega-3 fatty acids. In still other embodiments, the composition comprises between about 290 mg to about 350 mg of omega-3 fatty acids. In one embodiment, the composition comprises about 320 mg of omega-3 fatty acids. In certain embodiments, the one or more omega-3 fatty acids are EPA, DHA, or a combination thereof. In certain embodiments, the one or more omega-3 fatty acids are present as components of algal oil, or are derived from algal oil. It should be understood that if the composition comprises, for example, 320 mg of omega-3 fatty acids, and the one or more omega-3 fatty acids are present as a component of algal oil in the composition, the composition may comprise greater than 320 mg of algal oil such that the total omega-3 fatty acid content of the composition is 320 mg.

In certain, embodiments, the dietary supplement composition comprises one or more probiotics, wherein the probiotic content is between about 10 million CFUs (Colony-Forming Units) to about 15 billion CFUs, between about 10 million to about 12.5 billion CFUs, between about 10 million to about 10 billion CFUs, between about 10 million to about 5 billion CFUs, between about 10 million to about 4 billion CFUs, between about 10 million to about 3 billion CFUs, between about 10 million to about 2 billion CFUs, between about 10 million to about 1 billion CFUs, between about 100 million CFUs to about 15 billion CFUs, between about 100 million to about 12.5 billion CFUs, between about 100 million to about 100 billion CFUs, between about 100 million to about 5 billion CFUs, between about 100 million to about 4 billion CFUs, between about 100 million to about 3 billion CFUs, between about 100 million to about 2 billion CFUs, between about 100 million to about 1 billion CFUs, between about 1 billion to about 10 billion CFUs, between about 1 billion to about 5 billion CFUs, between about 1 billion to 4 billion CFUs, between about 2 billion to about 5 billion CUFs, or between about 2 billion to 3 billion CFUs. The one or more probiotics may comprise one or more spore-forming species, one or more non-spore-forming species, or any combinations thereof. In one embodiment, the one or more probiotics are spore-forming species. In another embodiment, the one or more probiotics are non-spore-forming species. In certain embodiments, the one or more probiotics comprise one or more Bacillus species, or one or more Bacillus strains, or a combination thereof. In other embodiments, the one or more probiotics comprise one or more Bifidobacterium species, or one or more Bifidobacterium strains, or a combination thereof. In certain embodiments, the one or more probiotics comprise one or more Lactobacillus species, one or more Lactobacillus strains, or a combination thereof. In certain embodiments, one or more probiotics comprise one or more cocci species, one or more cocci strains, or a combination thereof. In some embodiments, the beadlets comprise one or more probiotics. In certain embodiments, the mini-tabs comprise one or more probiotics. In another embodiment, the oil comprises one or more probiotics. In still a further embodiment, the beadlets or mini-tabs and oil independently comprise one or more probiotics.

In certain embodiments, the dietary supplement composition comprises between about 3.75 mg to about 11.25 mg, between about 6.75 mg to about 11.25 mg, between about 6.75 mg to about 10.5 mg, between about 6.75 mg to about 9.75 mg, between about 6.75 mg to about 9.375 mg, from about 6.75 mg to about 8.25 mg, or about 7.5 mg zinc. In some embodiments the composition comprises between about 6.75 mg to about 10.5 mg zinc. In other embodiments, the composition comprises between about 6.75 mg to about 9.75 mg zinc. In yet other embodiments, the composition comprises between about 6.75 mg to about 9.375 mg zinc. In still further embodiments, the composition comprises between about 6.75 mg to about 8.25 mg zinc. In one embodiment, the composition comprises about 7.5 mg zinc. The zinc may be in any suitable form, for examples as a zinc salt. In one embodiment, the zinc is zinc bisglycinate. It should be understood that if the composition comprises, for example, 7.5 mg of zinc, and the zinc is present in the form of a chemical compound comprising zinc, the composition may comprise greater than 7.5 mg of the zinc compound such that the total zinc content of the composition is 7.5 mg.

In certain embodiments, the dietary supplement composition comprises between about 35 mcg to about 300 mcg, between about 50 mcg to about 250 mcg, between about 75 mcg to about 210 mcg, between about 100 mcg to about 190 mcg, between about 112 mcg to about 180 mcg, between about 125 mcg to about 175 mcg, or about 150 mcg iodine. In some embodiments the composition comprises between about 75 mcg to about 210 mcg iodine. In other embodiments, the composition comprises between about 100 mcg to about 190 mcg iodine. In yet other embodiments, the composition comprises between about 112 mcg to about 180 mcg iodine. In still further embodiments, the composition comprises between about 125 mcg to about 175 mcg iodine. In one embodiment, the composition comprises about 150 mcg iodine. The iodine may be in any suitable form, for examples as one or more iodine salts. In one embodiment, the iodine is potassium iodide. It should be understood that if the composition comprises, for example, 150 mcg of iodine, and the iodine is present in the form of a chemical compound comprising iodine, the composition may comprise greater than 150 mcg of the iodine compound such that the total iodine content of the composition is 150 mcg.

In certain embodiments, the dietary supplement composition comprises between about 20 mcg to about 500 mcg, between about 25 mcg to about 400 mcg, between about 30 mcg to about 300 mcg, between about 45 mcg to about 200 mcg, between about 75 mcg to about 180 mcg, between about 90 mcg to about 150 mcg, or about 120 mcg chromium. In some embodiments the composition comprises between about 30 mcg to about 300 mcg chromium. In other embodiments, the composition comprises between about 45 mcg to about 200 mcg chromium. In yet other embodiments, the composition comprises between about 75 mcg to about 180 mcg chromium. In still further embodiments, the composition comprises between about 90 mcg to about 150 mcg chromium. In one embodiment, the composition comprises about 120 mcg chromium. The chromium may be in any suitable form, for examples as a chromium chelate. In one embodiment, the chromium is chromium histidinate. It should be understood that if the composition comprises, for example, 120 mcg of chromium, and the chromium is present in the form of a chemical compound comprising chromium, the composition may comprise greater than 120 mcg of the chromium compound such that the total chromium content of the composition is 120 mcg.

In certain embodiments, the dietary supplement composition comprises between about 20 mcg to about 400 mcg, between about 40 mcg to about 300 mcg, between about 45 mcg to about 200 mcg, between about 55 mcg to about 120 mcg, between about 60 mcg to about 90 mcg, between about 65 mcg to about 75 mcg, or about 70 mcg selenium. In some embodiments the composition comprises between about 40 mcg to about 300 mcg selenium. In other embodiments, the composition comprises between about 45 mcg to about 200 mcg selenium. In yet other embodiments, the composition comprises between about 55 mcg to about 120 mcg selenium. In still further embodiments, the composition comprises between about 25 mcg to about 75 mcg selenium. In one embodiment, the composition comprises about 70 mcg selenium. The selenium may be in any suitable form, for examples as an organic selenium compound. In one embodiment, the selenium is selenium L-methionate. It should be understood that if the composition comprises, for example, 120 mcg of selenium, and the selenium is present in the form of a chemical compound comprising selenium, the composition may comprise greater than 120 mcg of the selenium compound such that the total selenium content of the composition is 120 mcg.

In certain embodiments, the dietary supplement composition comprises between about 15 mg to about 1000 mg, between about 45 mg to about 750 mg, between about 60 mg to about 500 mg, between about 75 mg to about 300 mg, between about 90 mg to about 250 mg, between about 100 mg to about 150 mg, or about 120 mg vitamin C. In some embodiments the composition comprises between about 60 mg to about 500 mg vitamin C. In other embodiments, the composition comprises between about 75 mg to about 300 mg vitamin C. In yet other embodiments, the composition comprises between about 90 mg to about 250 mg vitamin C. In still further embodiments, the composition comprises between about 100 mg to about 150 mg vitamin C. In one embodiment, the composition comprises about 120 mg vitamin C. The vitamin C may be in any suitable form, for example as ascorbic acid, an ascorbate salt, or an ascorbate chelate. In one embodiment, the vitamin C is present as a vitamin C chelate. In one embodiment, the vitamin C is calcium ascorbate. It should be understood that if the composition comprises, for example, 120 mg of vitamin C, and the vitamin C is present in the form of a chemical compound comprising vitamin C, the composition may comprise greater than 120 mg of the compound such that the total vitamin C content of the composition is 120 mg.

In certain embodiments, the dietary supplement composition comprises between about 500 IU to about 30,000 IU, between about 1000 IU to about 20,000 IU, between about 1500 IU to about 15,000 IU, between about 1800 IU to about 12,000 IU, between about 2000 IU to about 11,000 IU, between about 3000 IU to about 10,000 IU, between about 4000 IU to about 7500 IU, between about 4500 IU to about 5500 IU, or about 5000 IU of one or more provitamin A carotenoids. In some embodiments, the composition comprises between about 1800 IU to about 2660 IU of one or more provitamin A carotenoids. In other embodiments, the composition comprises between about 1800 IU to about 2500 IU of one or more provitamin A carotenoids. In still other embodiments, the composition comprises between about 1800 IU to about 2200 IU of one or more provitamin A carotenoids. In one embodiment, the composition comprises about 2000 IU of one or more provitamin A carotenoids. In some embodiments, the one or more provitamin A carotenoids is derived from red palm oil. In some embodiments, the provitamin A carotenoid is beta-carotene, alpha-carotene, or cryptoxanthin. In some embodiments, the provitamin A is beta-carotene.

In some embodiments, the dietary supplement composition comprises between about 5 mg to about 20 mg, between about 5 mg to about 15 mg, between about 9 mg to about 15, between about 9 mg to about 14 mg, between about 9 mg to about 13 mg, between about 9 mg to about 11 mg, or about 10 mg of one or more carotenoids other than beta-carotene. For example, in some embodiments, the dietary supplement composition may comprise between about 5 mg to about 20 mg, between about 5 mg to about 15 mg, between about 9 mg to about 15, between about 9 mg to about 14 mg, between about 9 mg to about 13 mg, between about 9 mg to about 11 mg, or about 10 mg of alpha-carotene, cryptoxanthin, lycopene, or lutein, or any combinations thereof.

In certain embodiments, the dietary supplement composition comprises between about 25 mg to about 1000 mg, between about 50 mg to about 800 mg, between about 100 mg to about 750 mg, between about 200 mg to about 650 mg, between about 300 mg to about 600 mg, between about 450 mg to about 550 mg, or about 500 mg MCTs. In some embodiments the composition comprises between about 100 mg to about 750 mg MCTs. In other embodiments, the composition comprises between about 300 mg to about 600 mg MCTs. In yet other embodiments, the composition comprises between about 200 mg to about 650 mg MCTs. In still further embodiments, the composition comprises between about 550 mg to about 450 mg MCTs. In one embodiment, the composition comprises about 500 mg MCTs. The MCTs may be present in any suitable form, for example as a refined coconut oil. In one embodiment, the MCTs are present as coconut oil. It should be understood that if the composition comprises, for example, 500 mg of MCTs, and the MCTs are present in the form of a chemical compound or mixture (such as coconut oil) comprising MCTs, the composition may comprise greater than 500 mg of the MCT compound or mixture such that the total MCT content of the composition is 500 mg.

In certain embodiments, the dietary supplement composition comprises between about 0.5 mg to about 1000 mg, between about 0.8 mg to about 500 mg, between about 1.1 mg to about 100 mg, between about 1.2 mg to about 50 mg, between about 1.4 mg to about 25 mg, from about 1.5 mg to about 2.5 mg, or about 1.7 mg vitamin B1. In some embodiments the composition comprises between about 1.1 mg to about 100 mg vitamin B1. In other embodiments, the composition comprises between about 1.2 mg to about 50 mg vitamin B1. In yet other embodiments, the composition comprises between about 1.4 mg to about 25 mg vitamin B1. In still further embodiments, the composition comprises between about 1.5 mg to about 2.5 mg vitamin B1. In one embodiment, the composition comprises about 120 mg vitamin B1. The vitamin B1 may be in any suitable form, for example as thiamin diphosphate. In one embodiment, the vitamin B1 is benfotiamine. It should be understood that if the composition comprises, for example, 120 mg of vitamin B1, and the vitamin B1 is present in the form of a chemical compound comprising vitamin B1, the composition may comprise greater than 120 mg of the vitamin B1 compound such that the total vitamin B1 content of the composition is 120 mg.

In certain embodiments, the dietary supplement composition comprises between about 5 mg to about 500 mg, between about 10 mg to about 250 mg, between about 12 mg to about 150 mg, between about 14 mg to about 100 mg, between about 16 mg to about 50 mg, between about 18 mg to about 25 mg, or about 20 mg vitamin B3. In some embodiments the composition comprises between about 12 mg to about 150 mg vitamin B3. In other embodiments, the composition comprises between about 14 mg to about 100 mg vitamin B3. In yet other embodiments, the composition comprises between about 16 mg to about 50 mg vitamin B3. In still further embodiments, the composition comprises between about 18 mg to about 25 mg vitamin B3. In one embodiment, the composition comprises about 20 mg vitamin B3. The vitamin B3 may be in any suitable form, for examples as a niacinamide riboside. In one embodiment, the vitamin B3 is NADH. It should be understood that if the composition comprises, for example, 20 mg of vitamin B3, and the vitamin B3 is present in the form of a chemical compound comprising vitamin B3, the composition may comprise greater than 20 mg of the vitamin B3 compound such that the total vitamin B3 content of the composition is 20 mg.

In certain embodiments, the dietary supplement composition comprises between about 0.5 mg to about 500 mg, between about 0.75 mg to about 100 mg, between about 1.0 mg to about 50 mg, between about 1.2 mg to about 25 mg, between about 1.5 mg to about 10 mg, between about 1.7 mg to about 2.5 mg, or about 2.0 mg vitamin B6. In some embodiments the composition comprises between about 60 mg to about 500 mg vitamin B6. In other embodiments, the composition comprises between about 75 mg to about 300 mg vitamin B6. In yet other embodiments, the composition comprises between about 90 mg to about 250 mg vitamin B6. In still further embodiments, the composition comprises between about 100 mg to about 150 mg vitamin B6. In one embodiment, the composition comprises about 120 mg vitamin B6. The vitamin B6 may be in any suitable form, for examples as pyridoxal-5'-phosphate. In one embodiment, the vitamin B6 is pyridoxine hydrochloride. It should be understood that if the composition comprises, for example, 2.0 mg of vitamin B6, and the vitamin B6 is present in the form of a chemical compound comprising vitamin B6, the composition may comprise greater than 2.0 mg of the vitamin B6 compound such that the total vitamin B6 content of the composition is 2.0 mg.

It should be further understood that one or more of any of the nutrients may be present in more than one form. For example, one nutrient may be present as a mixture of salts, or may be present in one form encapsulated in a plurality of sucrosomes and in an additional form not encapsulated in a sucrosome.

A. Nutrient Ratios

The compositions as described herein may comprise any suitable ratio of two or more nutrients.

For example, in some embodiments, the composition comprises vitamin B12 and folate, and the weight ratio of vitamin B12 to folate is from about 4:900 to about 12:300. In other embodiments, the weight ratio of vitamin B12 to folate is from about 7:840 to about 11.2:540. In still other embodiments, the weight ratio of vitamin B12 to folate is from about 7:800 to about 10.64:540. In another embodiment, the weight ratio of vitamin B12 to folate is from about 7:750 to about 10:540. In one embodiment, the weight ratio of vitamin B12 to folate is from about 7:660 to about 9:540. In one embodiment, the weight ratio of vitamin B12 to folate is about 8:600. In another embodiment, the weight ratio of vitamin B12 to folate is from about 1:1000 to about 1:100. In still a further embodiment, the weight ratio of vitamin B12 to folate is from about 1:50 to about 1:10. In certain embodiments, the beadlets comprise the vitamin B12 and folate, for example in one or more nutrient layers. In some embodiments, the vitamin B12 is methylcobalamin. In some embodiments, the folate is a 5MTHF salt, for example 5MTHF glucosamine salt.

In some embodiments, the composition comprises iron and magnesium, and the weight ratio of iron to magnesium is from about 4:75 to about 12:25. In other embodiments, the weight ratio of iron to magnesium is from about 7:70 to about 11.2:45. In still other embodiments, the weight ratio of iron to magnesium is from about 7:66.5 to about 10.64:45. In another embodiment, the weight ratio of iron to magnesium is from about 7:62.5 to about 10:45. In one embodiment, the weight ratio of iron to magnesium is from about 7:55 to about 9:45. In one embodiment, the weight ratio of iron to magnesium is about 8:50. In another embodiment, the weight ratio of iron to magnesium is from about 1:400 to about 1:100. In still a further embodiment, the weight ratio of iron to magnesium is from about 3:75 to about 8:300. In certain embodiments, the beadlets or mini-tabs comprise the iron and magnesium, for example in one or more nutrient layers. In some embodiments, the iron is in the form of an iron salt, for example ferrous bisglycinate. In certain embodiments, the magnesium is in the form of a magnesium salt or a magnesium-sucrosome compound.

In some embodiments, the composition comprises boron and iron, and the weight ratio of boron to iron is from about 0.5:12 to about 1.5:4. In other embodiments, the weight ratio of boron to iron is from about 0.9:11.2 to about 1.4:7. In another embodiment, the weight ratio of boron to iron is from about 0.9:10.64 to about 1.33:7. In one embodiment, the weight ratio of boron to iron is from about 0.9:10 to about 1.25:7. In still other embodiments, the weight ratio of boron to iron is from about 0.9:9 to about 1.1:7. In one embodiment, the weight ratio of boron to iron is about 1:8. In another embodiment, the weight ratio of boron to iron is from about 1:27 to about 6:18. In still a further embodiment, the weight ratio of boron to iron is from about 1;3 to about 3:4. In certain embodiments, the beadlets comprise the boron and iron, for example in one or more nutrient layers. In some embodiments, the boron is in the form of a carbohydrate-boron complex, such as a fructoborate salt, for example calcium fructoborate. In some embodiments, the iron is in the form of an iron salt, for example ferrous bisglycinate.

In some embodiments, the composition comprises vitamin B12 and vitamin K, and the weight ratio of vitamin B12 to vitamin K is from about 4:135 to about 12:45. In other embodiments, the weight ratio of vitamin B12 to vitamin K is from about 7:126 to about 11.2:81. In still other embodiments, the weight ratio of vitamin B12 to vitamin K is from about 7:120 to about 10.64:81. In another embodiment, the weight ratio of vitamin B12 to vitamin K is from about 7:112.5 to about 10:81. In one embodiment, the weight ratio of vitamin B12 to vitamin K is from about 7:99 to about 9:81. In one embodiment, the weight ratio of vitamin B12 to vitamin K is about 8:90. In another embodiment, the weight ratio of vitamin B12 to vitamin K is from about 1:50 to about 1:12. In still a further embodiment, the weight ratio of vitamin B12 to vitamin K is from about 6:100 to about 18:100. In certain embodiments, the beadlets comprise the vitamin B12, for example in one or more nutrient layers, and the oil comprises the vitamin K. In some embodiments, the vitamin B12 is methylcobalamin. In some embodiments, the vitamin K is vitamin K2, for example MK-7.

In some embodiments, the composition comprises one or more omega-3 fatty acids and magnesium, and the weight ratio of omega-3 fatty acids to magnesium is from about 160:75 to about 480:25. In another embodiment, the weight ratio of omega-3 fatty acids to magnesium is from about 290:70 to about 450:45. In still other embodiments, the weight ratio of omega-3 fatty acids to magnesium is from about 290:66.5 to about 426:45. In another embodiment, the weight ratio of omega-3 fatty acids to magnesium is from about 290:62.5 to about 400:45. In one embodiment, the weight ratio of omega-3 fatty acids to magnesium is from about 290:55 to about 350:45. In one embodiment, the weight ratio of omega-3 fatty acids to magnesium is about 320:50. In another embodiment, the weight ratio of omega-3 fatty acids to magnesium is from about 2000:10 to about 250:50. In yet another embodiment, the weight ratio of omega-3 fatty acids to magnesium is from about 500:100 to about 640:250. In certain embodiments, the oil comprises the one or more omega-3 fatty acids, and the beadlets comprise the magnesium, for example in one or more nutrient layers. In some embodiments, the one or more omega-3 fatty acids are EPA, DHA, or a combination thereof. In certain embodiments, the one or more omega-3 fatty acids are present as components of algal oil, or are derived from algal oil. In certain embodiments, the magnesium is in the form of a magnesium salt or a magnesium-sucrosome compound.

In some embodiments, the composition comprises vitamin E and vitamin D, and the IU ratio of vitamin E to vitamin D is from about 5:3000 to about 15:1000. In other embodiments, the IU ratio of vitamin E to vitamin D is from about 9:2800 to about 14:1800. In another embodiment, the IU ratio of vitamin E to vitamin D is from about 9:2660 to about 13.3:1800. In one embodiment, the IU ratio of vitamin E to vitamin D is from about 9:2500 to about 12.5:1800. In certain embodiments, the IU ratio of vitamin E to vitamin D is from about 9:2200 to about 11:1800. In one embodiment, the IU ratio of vitamin E to vitamin D is about 10:2000. In another embodiment, the IU ratio of vitamin E to vitamin D is from about 10:4000 to about 30:400. In yet a further embodiment, the IU ratio of vitamin E to vitamin D is from about 30:2000 to about 20:600. In certain embodiments, the oil comprises the vitamin E and vitamin D. In one embodiment, the vitamin E is present as a mixture of tocopherols. In another embodiment, the vitamin D is present as vitamin D3.

In some embodiments, the composition comprises boron and magnesium, and the weight ratio of boron to magnesium is from about 0.5:75 to about 1.5:25. In another embodiment, the weight ratio of boron to magnesium is from about 0.9:70 to about 1.4:45. In other embodiments, the weight ratio of boron to magnesium is from about 0.9:66.5 to about 1.33:45. In still other embodiments, the weight ratio of boron to magnesium is from about 0.9:62.5 to about 1.25:45. In yet other embodiments, the weight ratio of boron to magnesium is from about 0.9:55 to about 1.1:45. In one embodiment, the weight ratio of boron to magnesium is about 1:50. In another embodiment, the weight ratio of boron to magnesium is from about 1:500 to about 3:30. In yet a further embodiment, the weight ratio of boron to magnesium is from about 2:350 to about 3:450. In certain embodiments, the beadlets comprise the boron and magnesium. In some embodiments, the boron is present in the form of a carbohydrate-boron complex, such as a fructoborate salt, for example calcium fructoborate. In certain embodiments, the magnesium is present as a magnesium salt, or a magnesium-sucrosome compound.

In some embodiments, the composition comprises vitamin K and boron, wherein the weight ratio of vitamin K to boron is from about 45:1500 to about 135:500. In another embodiment, the weight ratio of vitamin K to boron is from about 81:1400 to about 126:900. In other embodiments, the weight ratio of vitamin K to boron is from about 81:1330 to 120:900. In still other embodiments, the weight ratio of vitamin K to boron is from about 81:1250 to about 223.5:900. In yet other embodiments, the weight ratio of vitamin K to boron is from about 81:1100 to about 99:900. In one embodiment, the weight ratio of vitamin K to boron is about 90:1000. In another embodiment, the weight ratio of vitamin K to boron is from about 10:6000 to about 380:1000. In yet a further embodiment, the weight ratio of vitamin K to boron is from about 40:3000 to about 160:2000. In certain embodiments, the beadlets comprise the boron, and the oil comprises the vitamin K. In some embodiments, the boron is present in the form of a carbohydrate-boron complex, such as a fructoborate or borogluconate salt, for example calcium fructoborate or calcium borogluconate. In certain embodiments, the vitamin K is vitamin K2, such as MK-7.

In some embodiments, the composition comprises vitamin D3 and vitamin K, wherein the weight ratio of vitamin D3 to vitamin K is from about 0.025:0.135 to about 0.075: 0.045. In other embodiments, the weight ratio of vitamin D3 to vitamin K is from about 0.045:0.135 to about 0.075:0.081. In certain embodiments, the weight ratio of vitamin D3 to vitamin K is from about 0.045:0.12 to about 0.067:0.081. In still other embodiments, the weight ratio of vitamin D3 to vitamin K is from about 0.045:0.1125 to about 0.0625:0.081. In yet other embodiments, the weight ratio of vitamin D3 to vitamin K is from about 0.045:0.099 to about 0.055:0.081. In one embodiment, the weight ratio of vitamin D3 to vitamin K is about 0.05:0.09. In certain embodiment, the vitamin K is vitamin K2, for example MK-7.

In some embodiments, the composition comprises vitamin D3 and boron, wherein the weight ratio of vitamin D3 to boron is from about 0.025:1.5 to about 0.075:0.5. In other embodiments, the weight ratio of vitamin D3 to boron is from about 0.045:1.5 to about 0.075:0.9. In still other embodiments, the weight ratio of vitamin D3 to boron is from about 0.045:1.3 to about 0.075:0.9. In certain embodiments, the weight ratio of vitamin D3 to boron is from about 0.045:1.25 to about 0.067:0.9. In other embodiments, the weight ratio of vitamin D3 to boron is from about 0.045:1.1 to about 0.0625:0.9. In one embodiment, the weight ratio of vitamin D3 to boron is about 0.05:1. In some embodiments, the boron is present in the form of a carbohydrate-boron complex, such as a fructoborate or borogluconate salt, for example calcium fructoborate or calcium borogluconate.

The compositions provided herein may comprise combinations of nutrients, wherein certain nutrients are present in ratios as described above. For example, compositions may comprise boron, magnesium, and vitamin K, wherein the weight ratio of boron to magnesium is from about 0.5:75 to about 1.5:25, or about 0.9:55 to about 1.1:45; and the weight ratio of vitamin K to boron is from about 45:1500 to about 135:500, or about 81:1100 to about 99:900.

In another embodiment, the composition comprises vitamin D3, vitamin K, magnesium, and boron, wherein the weight ratio of vitamin D3 to vitamin K is from about 0.025:0.135 to about 0.075:0.045, or from about 0.045:0.099 to about 0.055:0.081, or about 0.05:0.09; the weight ratio of vitamin K to boron is from about 0.045:1.5 to about 0.135: 0.5, or about 0.081:1.1 to about 0.099:0.9, or about 0.09:1; and the weight ratio of magnesium to boron is from about 25:1.5 to about 75:0.5, or about 45:1.1 to about 55:0.9, or about 50:1. In some embodiments, the vitamin K is vitamin K2, for example MK-7. The boron may be present in the form of a carbohydrate-boron complex, such as a fructoborate or borogluconate salt, for example calcium fructoborate or calcium borogluconate. The magnesium may be present as a magnesium salt, or magnesium-sucrosome compound. In one embodiment, the composition comprises vitamin D3, vitamin K2 as MK-7, a magnesium-sucrosome compound, and boron as calcium fructoborate, wherein the weight ratio of vitamin D3 to vitamin K2 is about 0.05:0.09; the weight ratio of vitamin K2 to boron is about 0.09:1; and the weight ratio of magnesium to boron is about 50:1.

B. Other Nutrients

As described above, the composition may comprise at least two nutrients selected from the group consisting of B vitamins, boron, magnesium, zinc, probiotics, choline, iodine, chromium, selenium, Vitamin C, iron, vitamin K, vitamin D, vitamin E, one or more carotenoids, MCTs, and omega-3 fatty acids. In some variations, the composition comprises one or more additional nutrients, such as one or more additional vitamins, dietary minerals, or a combination thereof.

The composition may also be essentially free of one or more nutrients. For example, the composition may comprise less than 10 wt %, less than 8 wt %, less than 5 wt %, less than 3 wt %, less than 1 wt %, less than 0.5 wt %, less than 0.2 wt %, less than 0.1 wt %, less than 0.05 wt %, less than 0.01 wt %, or less than 0.001 wt % of one or more nutrients selected from the group consisting of vitamin A, vitamin B1, vitamin B2, vitamin B4, vitamin B6, calcium, pantothenate, biotin, vitamin C, copper, manganese, selenium, chromium, and molybdenum. In some embodiments, the composition is essentially free of retinol and retinol equivalents.

In one embodiment, the composition comprises less than 10 wt %, less than 8 wt %, less than 5 wt %, less than 3 wt %, less than 1 wt %, less than 0.5 wt %, less than 0.2 wt %, less than 0.1 wt %, less than 0.05 wt %, less than 0.01 wt %, or less than 0.001 wt % calcium. In certain embodiments, the composition comprises vitamin K, vitamin D, magnesium, and boron. Administering a composition comprising this combination of nutrients to a mammal, such as a human, may increase the absorption, utilization, and/or metabolism of calcium from the diet of the mammal without additional supplementation of calcium (e.g., through the administration of calcium in a gummy, tablet, capsule, soft-gel, powder, or other supplement form).

C. Administration

The composition may be formulated for administration to a mammal. In some embodiments, the mammal is a human. The composition may be formulated for administration to a woman, a man, or both women and men. The composition may be formulated for administration to a child, an adult, or a combination thereof. The composition may be formulated for administration to a female, a male, or both females and males. The composition may be formulated for children, adults, or seniors.

In some embodiments, the composition is formulated as a pre-natal supplement, for example for administration to a woman attempting to conceive or who is pregnant. In other embodiments, the composition is formulated as a post-natal supplement, for example for administration to a women who has given birth within the previous 1 month, 3 months, 6 months, 9 months, 12 months, 15 months, 18 months, 21 months, or 24 months. In some embodiments, the woman is breastfeeding. In certain embodiments, a post-natal supplement may be administered to a women at any point, or continuously, from immediately after childbirth until the earlier of stopping breastfeeding or two years following childbirth. In still other embodiments, the composition is formulated as a supplement for senior women, for example for administration to a woman who is about 50 years of age or greater. In still further embodiments, the composition is formulated as a supplement for adolescent women, for example for administration to a women between about 14 to about 18 years old. In other embodiments, the composition is formulated as a supplement for administration to children of any gender from about 8 to about 14 years of age. In some embodiments, the composition is formulated for a man. In certain embodiments, administration of the composition to a man may result in maintenance of prostate health and fertility (for example, good spermatozoa and semen quality).

The composition may comprise at least two, at least three, at least four, or at least five nutrients selected from the group consisting of B vitamins, boron, magnesium, iron, vitamin K, vitamin D, vitamin E, and omega-3 fatty acids. The B vitamins may be, for example, vitamin B12, or folate, or a combination thereof. In some variations, the composition comprises vitamin K, vitamin D, boron, and magnesium. In other variations, the composition comprises vitamin B12, folate, boron, magnesium, iron, vitamin K, vitamin D, vitamin E, and one or more omega-3 fatty acids. The composition may comprise vitamin B12, boron as a carbohydrate-boron complex, magnesium as a magnesium salt or a magnesium-sucrosome compound, iron as an iron salt, folate as a 5MTHF salt, vitamin K2, vitamin D, vitamin E, and one or more omega-3 fatty acids. In one embodiment, such a composition is formulated for administration to a woman. In certain embodiments, the woman is pre-menopausal. In some embodiments, the woman is pregnant or attempting to conceive. In certain embodiments, the woman has given birth within the previous 1 month, 3 months, 6 months, 9 months, 12 months, 15 months, 18 months, 21 months, or 24 months. In some embodiments, the woman is breastfeeding.

In some embodiments, the beadlets or mini-tabs comprises vitamin B12 as methylcobalamin, boron as calcium fructoborate, magnesium as a magnesium-sucrosome compound or magnesium salt, iron as ferrous bisglycinate, and folate as (6S)-5-methyltetrahydrofolate glucosamine salt; and the oil comprises vitamin K as menaquinone-7, vitamin D3, vitamin E as mixed tocopherols, and the omega-3 fatty acids docosahexanoic acid and eicosapentaenoic acid. In one embodiment, such a composition is formulated for administration to a woman. In certain embodiments, the woman is pre-menopausal. In some embodiments, the woman is pregnant or attempting to conceive. In certain embodiments, the woman has given birth within the previous 1 month, 3 months, 6 months, 9 months, 12 months, 15 months, 18 months, 21 months, or 24 months. In some embodiments, the woman is breastfeeding.

In some variations, each unit dose of the dietary supplement comprises between about 80 mcg to about 120 mcg, or between about 80 mcg to about 100 mcg vitamin K; between about 1800 IU to about 2500 IU, or between about 1800 IU to about 2200 IU vitamin D; between about 5 mcg to about 11 mcg, or between about 7 to about 9 mcg vitamin B12; between about 0.9 mg to about 1.1 mg boron; between about 9 IU to about 15 IU, or between about 9 IU to about 11 IU of vitamin E; between about 34 mg to about 65 mg, or between about 34 mg to about 50 mg, or between about 34 mg to about 42 mg, or between about 45 mg to about 65 mg, or between about 45 mg to about 55 mg magnesium; between about 500 mcg to about 2600 mcg, or between about 500 mcg to about 800 mcg, or between about 540 mcg to about 660 mcg, or between about 1800 mcg to about 2600 mcg, or between about 1800 mcg to about 2200 mcg of folate; between about 7 mg to about 24 mg, or between about 7 mg to about 9 mg, or between about 16 mg to about 24 mg, or between about 16 mg to about 20 mg iron; and between about 290 mg to about 350 mg of omega-3 fatty acids. In some embodiments, the composition is formulated for administration to a woman. In some embodiments, each unit dose of the dietary supplement comprises between about 1800 mcg to about 2600 mcg, or between about 1800 mcg to about 2200 mcg of folate; and between about 16 mg to about 24 mg, or between about 16 mg to about 20 mg iron, and is formulated for a woman who is pregnant or attempting to conceive. Each unit dose may comprise, for example, a plurality of beadlets or mini-tabs and oil as described herein contained within one capsule, or two capsules, or three or more capsules.

In one embodiment, the beadlets or mini-tabs consist essentially of methylcobalamin, calcium fructoborate, a magnesium-sucrosome compound, ferrous bisglycinate, (6S)-5-methyltetrahydrofolate glucosamine salt, cellulose, citric acid, corn starch, corn zein, dicalcium phosphate, lecithin, and silica; and the oil consists essentially of menaquinone-7, vitamin D3, mixed tocopherols, algal oil, ascorbyl palmitate, d-alpha-tocopherol, one or more plant oils, medium chain triglycerides, silica, and one or more odorant or flavorant agents. The one or more plant oils may be selected from the group consisting of coconut oil and sunflower oil. The odorant or flavorant agent may be vanilla flavor, peppermint oil, peppermint flavor, ginger flavor, ginger oil, grapefruit flavor, grapefruit oil, lemon flavor, lemon oil, lime flavor, lime oil, orange flavor, or orange oil, or any combinations thereof. In one embodiment, the odorant or flavorant agent is vanilla flavor or peppermint oil. In one embodiment, such a composition is formulated for administration to a woman. In certain embodiments, the woman is pre-menopausal. In some embodiments, the woman is pregnant or attempting to conceive.

The composition may comprise at least two, at least three, at least four, or at least five nutrients selected from the group consisting of B vitamins, boron, magnesium, vitamin K, vitamin D, vitamin E, chromium, one or more carotenoids, and omega-3 fatty acids. The B vitamins may be, for example, vitamin B12, or folate, or a combination thereof. In some variations, the composition comprises vitamin K, vitamin D, boron, and magnesium. In other variations, the composition comprises vitamin B12, folate, boron, magnesium, vitamin K, vitamin D, vitamin E, chromium, one or more carotenoids, and one or more omega-3 fatty acids. The composition may comprise vitamin B12, boron as a carbohydrate-boron complex, magnesium as a magnesium salt or a magnesium-sucrosome compound, folate as a 5MTHF salt, vitamin K2, vitamin D, vitamin E, chromium as a compound comprising Cr', one or more carotenoids, and one or more omega-3 fatty acids. In one embodiment, such a composition is formulated for administration to a woman. In certain embodiments, the woman is post-menopausal, for example a woman who has not has menstrual periods for at least a year.

In some embodiments, the beadlets or mini-tabs comprises vitamin B12 as methylcobalamin, boron as calcium fructoborate, magnesium as a magnesium-sucrosome compound, chromium as a compound comprising Cr', and folate as (6S)-5-methyltetrahydrofolate glucosamine salt; and the oil comprises vitamin K as menaquinone-7, vitamin D3, vitamin E as mixed tocopherols, one or more carotenoids, and the omega-3 fatty acids docosahexanoic acid and eicosapentaenoic acid. In one embodiment, such a composition is formulated for administration to a woman. In certain embodiments, the woman is post-menopausal.

In another embodiment, the composition comprises at least two, at least three, at least four, at least five, or more nutrients selected from the group consisting of B vitamins, boron, magnesium, zinc, vitamin K, vitamin D, vitamin E, and omega-3 fatty acids. In some embodiments, the composition further comprises one or more nutrients selected from the group consisting of chromium, selenium, and one or more carotenoids. The B vitamins may be, for example, vitamin B12, vitamin B1, vitamin B3, vitamin B6, folate, or any combinations thereof. In some variations, the composition comprises vitamin K, vitamin D, boron, magnesium, zinc, omega-3 fatty acids, and one or more B vitamins selected from the group consisting of vitamin B12, vitamin B1, vitamin B3, vitamin B6, and folate. In some variations, the composition further comprises selenium, chromium, or one or more carotenoids, or any combinations thereof. In other variations, the composition comprises vitamin B12, vitamin B1, vitamin B3, vitamin B6, folate, boron, magnesium, vitamin K, vitamin D, vitamin E, chromium, selenium, one or more carotenoids, and one or more omega-3 fatty acids. The composition may comprise vitamin B12, vitamin B1, vitamin B3 as niacinamide riboside, vitamin B6, folate as a 5-MTHF salt, boron as a carbohydrate-boron complex, magnesium as a magnesium salt or a magnesium-sucrosome compound, zinc as a zinc salt, vitamin K2, vitamin D, vitamin E, a compound that comprises Cr', a compound that comprises selenium, one or more carotenoids, and one or more omega-3 fatty acids. In one embodiment, such a composition is formulated for administration to a man.

In some embodiments, the beadlets or mini-tabs comprises vitamin B12 as methylcobalamin, folate as (6S)-5-methyltetrahydrofolate glucosamine salt, boron as calcium fructoborate, magnesium as a magnesium-sucrosome compound or a magnesium salt, zinc as a zinc salt; and the oil comprises vitamin K as menaquinone-7, vitamin D3, vitamin E as mixed tocopherols, one or more carotenoids, and the omega-3 fatty acids docosahexanoic acid and eicosapentaenoic acid. In some embodiments, the beadlets further comprise vitamin B1, vitamin B3, vitamin B6, selenium as L-selenocysteine or L-selenomethionine, or chromium as a compound comprising $Cr^{3+}$, or any combinations thereof. In certain embodiments, the oil further comprises one or more carotenoids. In some embodiments, the composition is formulated for administration to a man.

In certain embodiments, each unit dose comprises between about 80 mcg to about 120 mcg, or between about 80 mcg to about 100 mcg vitamin K; between about 1800 IU to about 2500 IU vitamin D; between about 14 mcg to about 21 mcg, or between about 14 mcg to about 18 mcg vitamin B12; between about 1.8 mg to about 2.6 mg, or about 1.8 mg to about 2.2 mg boron; between about 18 IU to about 26 IU, or between about 18 IU to about 22 IU of vitamin E; between about 34 mg to about 50 mg, or between about 34 mg to about 42 mg magnesium; between about 500 mcg to about 800 mcg, or about 540 mcg to about 660 mcg of folate; between about 6.75 mg to about 9.75 mg, or about 6.75 mg to about 8.25 mg zinc; and between about 315 mg to about 450 mg, or about 315 mg to about 385 mg of omega-3 fatty acids. In some embodiments, such a composition is formulated for administration to a man. Each unit dose may comprise, for example, a plurality of beadlets or mini-tabs and oil as described herein contained within one capsule, or two capsules, or three or more capsules.

In some embodiments, the beadlets or mini-tabs comprises vitamin B12 as methylcobalamin, folate as (6S)-5-methyltetrahydrofolate glucosamine salt, boron as calcium fructoborate, magnesium as a magnesium-sucrosome compound or a magnesium salt, and zinc as a zinc salt; and the oil comprises vitamin K as menaquinone-7, vitamin D3, vitamin E as mixed tocopherols, and the omega-3 fatty acids docosahexanoic acid and eicosapentaenoic acid. In some embodiments, the composition is formulated for administration to a man.

The composition may be formulated for daily administration. Daily administration may include administration once, twice, three times, four times, or more per day. In one embodiment, the composition is formulated for administration once per day, such as once per 24 hours, or once per time period from 12 am to 11:59 pm on the same calendar date. The composition may be formulated for administration in any suitable number of capsules. For example, the composition may be formulated for administration of one capsule, two capsules, three capsules, four capsules, five capsules, or more, wherein the one, two, three, four, five, or more capsules are administered once, twice, three times, four times, or more per day. In one embodiment, the composition is formulated for administration of two capsules, once per day.

VII. Methods of Producing

The compositions provided herein may be produced by any suitable methods known in the art.

In certain embodiments, the beadlets are produced by applying one or more layers to a solid core. In one embodiment, a plurality of generally spherical cores are placed in a rotating drum. The drum is rotated and in some embodiments warmed to a certain temperature to facilitate the drying of layers. The components of the first layer (e.g., one or more excipients, one or more nutrients, or any combinations thereof) are combined with water to form a homogenous flowable slurry, which is then sprayed into the rotating drum while it rotates to coat the plurality of cores. The flowable slurry may comprise one or more nutrients, excipients, or a combination thereof. In certain embodiments, wherein the flowable slurry comprises one or more nutrients and one or more excipients, the one or more excipients are combined with the one or more nutrients to form the flowable slurry. In other embodiments, the one or more excipients are associated with the one or more nutrients, such as, for example, a nutrient compound that comprises one or more excipients.

Spraying is suspended for a period of time and the drum is rotated until the layer is sufficiently dry for a subsequent layer to be added. It should be understood that when the subsequent layer is added, the first layer may still comprise water. This process may be repeated with different slurries to build different layers on the core. The penultimate layer may comprise magnesium, for example a magnesium oxide or magnesium salt, to provide a light-colored or white appearance to the beadlet. The inclusion of magnesium in at least one layer may provide a light-colored or white appearance without requiring the use of a titanium-containing excipient, such as titanium oxide. In some embodiments, the initial layer surrounding the core comprises one or more light sensitive nutrients, such as one or more nutrients that degrades or is otherwise negatively affected by exposure to light for a period of time. In embodiments, where at least one layer of the beadlet is opaque (such as a layer comprising certain magnesium compounds), at least one opaque layer is applied after applying one or more layers comprising one or more light sensitive nutrients. Light sensitive nutrients may include, for example, certain forms of vitamin B12 and folate. A final layer may be applied, wherein the final layer comprises one or more excipients but is essentially free of nutrients miscible in aqueous solution. This final layer may be dried in such a way as to provide a barrier between the oil and the one or more nutrients in the one or more coatings of the beadlets in the final composition. In some embodiments, the final layer comprises protein, such as corn zein.

In certain embodiments, the mini-tabs are produced by compressing a mixture of one or more nutrients and one or more excipients to produce solid base forms. The components of the solid base forms (e.g., one or more excipients, one or more nutrients, or any combinations thereof) are combined to form a powder or granule mixture, which may be filled into a dye mold and compressed. In some embodiments, a plurality of solid base forms are produced at once (e.g., with a dye mold that has multiple mold forms), while in other embodiments, solid base forms are produced one at a time sequentially. In certain embodiments, wherein the solid base forms comprise one or more excipients and one or more nutrients, the one or more excipients are combined with the one or more nutrients to form the mixture that is compressed. In other embodiments, the one or more excipients are associated with the one or more nutrients, such as, for example, a nutrient compound that comprises one or more excipients. In some embodiments, one or more coating layers may be applied to the plurality of solid base forms to produce the mini-tabs. This may be done, for example, by rotating the mini-tabs in a drum and spraying the plurality of solid base forms with a solution or slurry of one or more excipients, then suspending spraying and rotating the drum to dry the layer. In some embodiments, a plurality of layers are applied. A final layer may be applied (which may be the only layer), wherein the final layer comprises one or more excipients but is essentially free of nutrients miscible in aqueous solution. This final layer may be dried in such a way as to provide a barrier between the oil and the one or more nutrients of the mini-tabs in the final composition. In some embodiments, the final layer comprises protein, such as corn zein. In certain embodiments, for nutrient supplement compositions comprising one or more water-miscible probiotics, incorporating the probiotics into mini-tabs by compressing a powder or granule mixture may result in better stability and/or maintain greater activity of the probiotics as compared to incorporating the probiotics into one or more nutrient layers of beadlets by the spraying of a probiotic-containing solution or slurry.

In certain embodiments, the components of the oil are combined to produce the oil under an inert atmosphere, for example under nitrogen. The oil may be stored under an inert atmosphere, such as nitrogen, for example prior to being combined with beadlets or mini-tabs. In embodiments wherein the composition is contained in one or more capsules, the oil may be stored under an inert atmosphere (such as nitrogen) prior to encapsulation, and during encapsulation may also be performed under inert atmosphere, such as under nitrogen gas. In certain embodiments, oxygen is prevented from contacting the oil during at least one or all of being produced from the components, storage before encapsulation, or during the encapsulation process.

VIII. Capsule

In some embodiments, the composition is contained in one or more capsules. For example, the composition may be encapsulated in one, two, three, four, five, six, or more capsules. In certain embodiments, the composition is contained in two capsules. In some embodiments, the composition is contained in one capsule. The capsules may be prepared from any suitable materials.

The composition may be contained in one or more extended release capsules that delay or extend the release of the capsule contents. For example, extended release capsules may reduce the amount of capsule contents released in the stomach, such that the majority or all of the contents are released in the digestive system after the capsule passes through the stomach. The use of a delayed release capsule may increase absorption of the nutrients contained therein, decrease unwanted interactions of the nutrients contained therein, or both, by releasing nutrients where they are optimally absorbed in the gastrointestinal tract. In some variations, the capsules comprise an extended release coating. Releasing nutrients past the stomach may prevent exposure of the nutrients to the low pH of the stomach, which can damage certain nutrients or cause them to undergo one or more chemical reactions. In addition, stomach acid can cause unwanted interactions between one or more nutrients or excipients that do not occur at the pH of the small intestine.

The one or more capsules may comprise one or more polymers, such as hydroxypropyl methylcellulose (hypromellose), gellan gum, pullalan, or any combinations thereof. The one or more capsules may comprise an excipient, such as one or more binders, fillers, diluents, lubricants, or any combinations thereof. In some embodiments, the capsules comprise hypromellose, gellan gum, and silica. In some embodiments, the one or more capsules consist essentially of hypromellose, gellan gum, and silica.

In certain embodiments, the one or more capsules are essentially free of ingredients derived from animals. For example, the one or more capsules may comprise less than 1 wt %, less than 0.1 wt %, or less than 0.01 wt % gelatin. The one or more capsules may be essentially free of gelatin.

The one or more capsules may be translucent. In some embodiments, the one or more capsules are transparent.

IX. Insert

Also provided herein is a scented insert. Said scented insert may be, for example, included in a container with a composition as described herein. Including a scented insert with the composition may associate a desirable odor with the composition or reduce the perception of an undesirable odor, which may increase a subject's compliance with a dosing regimen. For example, the composition may comprise algal oil, which may impart an undesirable "fishy" odor. Including a scented insert with a composition that comprises algal oil may decrease the perception of an undesirable "fishy" odor, which may in turn increase compliance with the dosing regimen of the dietary supplement composition.

In some embodiments, the insert comprises polymer and an odorant agent. The odorant agent may be derived from natural sources. In some embodiments, the odorant agent comprises a plant oil, one or more compounds derived from plants, or an oil comprising one or more compounds derived from a plant. In some embodiments, the odorant agent is a plant oil, one or more compounds derived from plants, or an oil comprising one or more compounds derived from a plant. In some embodiments, the odorant agent comprises an oil, extract, or scent of berry, cherry, cinnamon, clove, ginger, grapefruit, lemon, lime, nutmeg, or orange, or any combinations thereof. In certain embodiments, the odorant agent comprises a mint oil or mint extract. In one embodiment, the mint is peppermint. In one embodiment, the odorant agent is derived from *Mentha piperita* L. The scented insert may comprise up to 1%, up to 3%, up to 5%, up to 7%, up to 10%, up to 12%, up to 15%, or up to 20% of the odorant agent by weight. In certain embodiments, the scented insert comprises between 1% to 20%, between 5% to 15%, between 8% to 12%, or between 9% to 11% of the odorant agent by weight. In certain embodiments, the scented insert comprises about 10% of the odorant agent by weight.

In some embodiments, the polymer is a copolymer. The polymer may comprise vinyl acetate. The polymer may be a vinyl acetate copolymer. The polymer may comprise ethylene. In one embodiment, the polymer is ethylene vinyl acetate. The scented insert may comprise up to 99%, up to 97%, up to 95%, up to 92%, up to 90%, up to 88%, up to 85%, or up to 80% polymer by weight. In certain embodiments, the scented insert comprises from 99% to 80%, from 95% to 85%, from 92% to 88%, or from 91% to 89% polymer by weight. In certain embodiments, the scented insert comprises about 90% polymer by weight.

In one embodiment, the scented insert consists essentially of odorant agent and polymer.

The scented insert may be any suitable shape. The insert may generally have the shape of a polygon with three, four, five, six, seven, eight, nine, ten, eleven, twelve, thirteen, fourteen, fifteen, or more sides. The insert may be a triangle; quadrilateral, such as a square, rectangle, rhombus, parallelogram, trapezoid, rhomboid, kite; a pentagon; a hexagon; a heptagon; a octagon; a nonagon; a decagon; a ring; a prism, such as a cube; a sphere; a pyramid, such as a right pyramid, a rectangular pyramid, a rhombic pyramid, or a star pyramid; a cone; a torus; a cylinder; a letter; a symbol; or a word. The insert may be in the shape of a star, for example a three-pointed star, four-pointed star, five-pointed star, six-pointed star, seven-pointed star, eight-pointed star, nine-pointed star, ten-pointed star, eleven-pointed star, twelve-pointed star, thirteen-pointed star, fourteen-pointed star, fifteen-pointed star, or a star with greater than fifteen points. The star may be symmetrical, or may not have a plane of symmetry. The insert may be generally round, for example be circular or ovoid. In some embodiments, the insert is shaped to emulate another object, for example an animal, plant, or inanimate object. In some embodiments, the insert comprises one or more holes or cutouts.

The insert may have a generally consistent thickness, for example having a thickness that deviates less than 10%, less than 5%, less than 2%, less than 1%, or less than 0.5%. In other embodiments, the insert comprises at least one point that deviates greater than 15%, greater than 20%, greater than 25%, greater than 30%, or greater than 35% in thickness from at least one other point. In some variations, the insert is relatively flat. In other variations, the insert is generally not flat. The insert may comprise one or more letters or symbols, for example located on one or more surfaces of the insert. The one or more letters or symbols may be embossed, punched, or etched into the surface.

The insert may be translucent. In some embodiments, the insert is transparent.

X. Packaging

The compositions provided herein may be packaged in any suitable container. The container may be, for example, a bottle or a jar. The container may be of any suitable material, such as plastic or glass. In some embodiments, the container comprises a lid, for example a cap, such as a snap-on cap or a screw top cap. In some embodiments, the lid is fully removable, for example, the lid may be completely separated from the container. In other embodiments, the lid may be connected to the container, for example by a piece of material that is attached to both the cap and the container, such that when the cap is removed from the opening of the container it is still connected to the container.

In some embodiments, the container comprises one or more plastics. The container may be essentially free of one or more bisphenol compounds. In one embodiment, the container is essentially free of bisphenol A. The container may be any suitable color, or may comprise a plurality of colors, or may be transparent or translucent. In some embodiments, at least a portion of the bottle is transparent or translucent. In one embodiment, the container is transparent. In some embodiments, the container comprises a bottle and a removable screw-top lid, wherein the bottle and lid comprise plastic and are essentially free of bisphenol A. In one embodiment, the bottle is transparent and the lid is white.

The container may further comprise one or more markings, such as a label or design. The markings may comprise one or more words, symbols, instructions, slogans, or combinations thereof. The one or more markings may be any suitable color, or a plurality of colors. In one embodiment, the markings are white.

As described above, in some embodiments the container comprises a scented insert. For example, a scented insert may be included inside the bottle, along with the composition.

The container may be further packaged in one or more additional containers. In some embodiments, the additional container is a box, such as a cardboard box, for example a corrugated cardboard box. For example, in some embodiments the composition is packaged in a container comprising a bottle and a removable screw-top lid, wherein the container is further packaged in an additional container comprising a cardboard box. The additional container may be any suitable color or shape, and may comprise one or more markings. In some embodiments, the additional container is a cardboard box comprising an attached lid that partially tucks into the base, wherein the box comprises a white exterior and a yellow interior, and one or more markings. In some embodiments, the composition is contained in one more transparent capsules.

The packaging may further comprise instructions, for example one or more pamphlets, sheets, booklets, or other written media. The instructions may be made of any suitable material, such as paper.

Provided herein is a kit, comprising a dietary nutrient composition as described herein, and a container. In some embodiments, the kit further comprises instructions. In certain embodiments, the composition is contained within one or more capsules; and the one or more capsules are packaged in the container. In some embodiments, the container comprises a bottle and a removable screw-top lid, wherein the container comprises plastic. In certain embodiments, the one or more capsules are transparent. In still other embodiments, the one or more capsules are essentially free of gelatin. In some embodiments, the kit further comprises a scented insert, wherein the scented insert is located within the container. The scented insert may be translucent. In some embodiments, the container is further packaged within an additional container, wherein additional container comprises a cardboard box. In certain embodiments, the kit further comprises instructions. In some embodiments, the composition is formulated for administration to women. In one embodiment, the composition is formulated for daily administration.

In one embodiment, provided herein is a kit, comprising a composition comprising:
 a plurality of beadlets and oil, as described herein;
 one or more capsules, wherein the composition is contained within the one or more capsules, and the one or more capsules are transparent and essentially free of gelatin; and
 a container comprising a bottle and a removable screw-top lid, wherein the container comprises plastic and is essentially free of bisphenol A, the bottle is transparent, the one or more capsules are packaged within the container, and the container comprises a scented insert wherein the scented insert is inside the bottle.

In another embodiment, provided herein is a kit, comprising a composition comprising:
 a plurality of mini-tabs and oil, as described herein;
 one or more capsules, wherein the composition is contained within the one or more capsules, and the one or more capsules are transparent and essentially free of gelatin; and
 a container comprising a bottle and a removable screw-top lid, wherein the container comprises plastic and is essentially free of bisphenol A, the bottle is transparent, the one or more capsules are packaged within the container, and the container comprises a scented insert wherein the scented insert is inside the bottle.

In some embodiments, the scented insert is translucent. In other embodiments, the plurality of beadlets are white or light colored. In further embodiments, the oil is translucent. In still further embodiments, the container is further packaged within an additional container, wherein additional container comprises a cardboard box. In other embodiments, the kit further comprises instructions. In certain embodiments, the composition is formulated for administration to women. In one embodiment, the composition is formulated for once daily administration to women, and is contained within two capsules. In a further embodiment, the oil comprises one or more odorant agents.

EXAMPLES

The following Examples are merely illustrative and are not meant to limit any aspects of the present disclosure in any way.

Example 1: Preparation of Beadlets

This example describes the production of a plurality of beadlets, wherein the beadlets comprise at least one nutrient that is miscible in aqueous solution.

Generally spherical microcrystalline cellulose cores were placed in a rotating drum. The drum was rotated and warmed to a predetermined temperature to facilitate the drying of layers. The components of the first layer (excipients and nutrients) were combined with water to form a homogenous flowable slurry, which was then sprayed into the rotating drum while it rotated to coat the MCC cores. Spraying was suspended for a period of time and the drum was rotated until the initial layer was sufficiently dry for a subsequent layer to be added. The subsequent layers were then applied to the cores in a similar manner, using a different mixture of excipients and nutrients to prepare a slurry, spraying the slurry into the rotating drum, and drying the coated cores. The second-to-last layer included a magnesium-sucrosome compound to provide a light-colored or white appearance to the beadlet. The final layer included corn zein, and was dried in such a way as to provide a barrier between the oil and the nutrients in the coatings of the beadlets.

Example 2: Women's Daily Formulation

This example describes the preparation and components of an exemplary dietary supplement composition formulated for once daily administration to women. This exemplary composition is encapsulated, wherein two capsules comprise one daily dose of the nutrient composition.

The components of the beadlets, oil, and capsules were tested by Quality Control prior to manufacturing. To produce the oil, the oil ingredients were assembled and blended together in an appropriate container (kettle) under a nitrogen atmosphere. Automated robotic containers with WiFi capability overseen by production personnel were used to add, weigh, and blend the oil components, and to transport the finished oil to the encapsulation machine. The beadlets were prepared according to Example 1.

Encapsulation of beadlets and oil into was performed under a nitrogen atmosphere. Capsule halves and beadlets were loaded into separate hoppers that feed into the encapsulation machine. Oil was pumped from the automated containers directly into the encapsulation machine, without being exposed to air. Capsule halves were placed into cassettes, and then were filled with beadlets to the specified amount. Oil was then added to the capsules in the specified amount and time allowed for the beadlets to settle into the oil, with agitation to remove bubbles and ensure that the beadlets and oil would fit into each capsule. The upper capsule half was added and the capsule was closed. Closed capsules entered a banding/sealing unit that sealed the capsules, preferably with a band of the same material as the capsule to prevent leakage and to provide an airtight seal. Capsules were inspected and sent to Quality Control quarantine for testing before being released for administration to a subject.

The quantity of nutrients per dosage (of two capsules) is listed in Table 1 below. Size 0 vegetarian, delayed-release capsules (DRcaps® Acid Resistant Capsules) made by Capsugel® were used for this formulation. Other capsule sizes and/or gelatin capsules could also be used to encapsulate the formulation below.

TABLE 1

Nutrient composition formulated for women.

| Nutrient | Amount per serving | % Daily Value |
| --- | --- | --- |
| Vitamin D (as cholecalciferol) | 2000 IU | 500 |
| Vitamin E (as alpha tocopherol from mixed tocopherols) (from *Brassica napus*) (seed) | 10 IU | 33 |
| Vitamin K (as menaquinone-7) | 90 mcg | 112 |
| Folate (as 6S-5-methyltetrahydrofolate glucosamine salt) | 600 mcg | 150 |
| Vitamin B12 (as methylcobalamin) | 8 mcg | 133 |
| Iron (as ferrous bisglycinate) | 8 mg | 44 |
| Magnesium (as Dimagnesium malate) | 38 mg | 8 |
| Boron (as calcium fructoborate) | 1 mg | ** |
| Omega-3 Fatty Acids (from *Schizochytrium* spp.) (whole microalgae) | 320 mg | ** |

Other ingredients: Beadlets (cellulose, nonGMO corn zein), delayed release vegetarian capsule (hypromellose, gellan gum), silica, vanilla flavor, peppermint oil Example 3: Men's Daily Formulation This example describes the components of an exemplary dietary supplement composition formulated for once daily administration to men. This exemplary composition could be encapsulated, wherein two capsules comprise one daily dose of the nutrient composition. This formulation could be prepared according to the procedure of Example 2 above. The quantity of nutrients per dose (for example, two capsules) is listed in Table 2 below.

TABLE 2

Exemplary nutrient composition formulated for men.

| Nutrient | Amount per serving | % Daily Value |
| --- | --- | --- |
| Vitamin A (as provitamin A beta carotene) | 5000 IU | 100 |
| Vitamin D (as cholecalciferol) | 2000 IU | 500 |
| Vitamin E (as alpha tocopherol from mixed tocopherols) (from *Brassica napus*) (seed) | 20 IU | 6 |
| Vitamin K (as menaquinone-7) | 90 mcg | 112 |
| Folate (as 6S-5-methyltetrahydrofolate glucosamine salt) | 600 mcg | 150 |
| Vitamin B12 (as methylcobalamin) | 16 mcg | 266 |
| Zinc (as zinc bisglycinate) | 7.5 mg | 5044 |
| Magnesium (as Dimagnesium malate) | 38 mg | 8 |
| Boron (as calcium fructoborate) | 2 mg | ** |

TABLE 2-continued

Exemplary nutrient composition formulated for men.

| Nutrient | Amount per serving | % Daily Value |
| --- | --- | --- |
| Mixed carotenoids (alpha carotene, lutein, lycopene) | 10 mg | ** |
| Omega-3 Fatty Acids (from *Schizochytrium* spp.) (whole microalgae) | 350 mg | ** |

Other ingredients: Beadlets (cellulose, nonGMO corn zein), delayed release vegetarian capsule (hypromellose, gellan gum), silica Enumerated Embodiments Embodiment 1. A daily women's health dietary supplement comprising a plurality of beadlets and oil, wherein:

the beadlets are solid, and comprise one or more nutrients miscible in aqueous solution selected from the group consisting of vitamin B12, boron, magnesium, iron, and folate; and the oil is liquid, and comprises one or more fat-soluble nutrients selected from the group consisting of vitamin K, vitamin D, vitamin E, and omega-3 fatty acids.

Embodiment 2. The daily women's health dietary supplement of Embodiment 1, wherein the beadlets comprise vitamin B12 and folate, and the weight ratio of vitamin B12 to folate is from about 7:660 to about 9:540.

Embodiment 3. The daily women's health dietary supplement of Embodiment 1 or 2, wherein the beadlets comprise iron and magnesium, and the weight ratio of iron to magnesium is from about 7:55 to about 9:45.

Embodiment 4. The daily women's health dietary supplement of any one of Embodiments 1 to 3, wherein the beadlets comprise boron and iron, and the weight ratio of boron to iron is from about 0.9:9 to about 1.1:7.

Embodiment 5. The daily women's health dietary supplement of any one of Embodiments 1 to 4, wherein beadlets comprise vitamin B12, the oil comprises vitamin K, and the weight ratio of vitamin B12 to vitamin K is from about 7:100 to about 9:80.

Embodiment 6. The daily women's health dietary supplement of any one of Embodiments 1 to 5, wherein oil comprises omega-3 fatty acids, the beadlets comprise magnesium, and the weight ratio of omega-3 fatty acids to magnesium is from about 290:55 to about 350:45.

Embodiment 7. The daily women's health dietary supplement of any one of Embodiments 1 to 6, wherein the oil comprises vitamin E and vitamin D, and the IU ratio of vitamin E to vitamin D is from about 9:2200 to about 11:1800.

Embodiment 8. The daily women's health dietary supplement of any one of Embodiments 1 to 7, wherein the beadlets comprise boron and magnesium, and the weight ratio of boron to magnesium is from about 0.9:55 to about 1.1:45.

Embodiment 9. The daily women's health dietary supplement of any one of Embodiments 1 to 8, wherein the oil comprises vitamin K, the beadlets comprise boron, and the weight ratio of vitamin K to boron is from about 80:1100 to about 100:900.

Embodiment 10. The daily women's health dietary supplement of any one of Embodiments 1 to 9, wherein the beadlets comprise boron and magnesium, and the oil comprises vitamin D and vitamin K.

Embodiment 11. The daily women's health dietary supplement of any one of Embodiments 1 to 10, wherein the beadlets comprise vitamin B12, boron, magnesium, iron, and folate; and the oil comprises vitamin K, vitamin D, vitamin E, and omega-3 fatty acids.

Embodiment 12. The daily women's health dietary supplement of any one of Embodiments 1 to 11, wherein: the beadlets comprise vitamin B12 as methylcobalamin, boron as calcium fructoborate, magnesium as a magnesium-sucrosome compound, iron as ferrous bisglycinate, and folate as (6S)-5-methyltetrahydrofolate glucosamine salt; and the oil comprises vitamin K as menaquinone-7, vitamin D3, vitamin E as mixed tocopherols, and the omega-3 fatty acids docosahexanoic acid and eicosapentaenoic acid.

Embodiment 13. The daily women's health dietary supplement of any one of Embodiments 1 to 12, wherein: the beadlets consist essentially of methylcobalamin, calcium fructoborate, a magnesium-sucrosome compound, ferrous bisglycinate, (6S)-5-methyltetrahydrofolate glucosamine salt, cellulose, citric acid, corn starch, corn zein, tricalcium phosphate, lecithin, rice starch, and silica; and the oil consists essentially of menaquinone-7, vitamin D3, mixed tocopherols, algal oil comprising omega-3 fatty acids, ascorbyl palmitate, d-alpha-tocopherol, coconut oil, medium chain triglycerides, silica, sunflower oil, and one or more odorant agents.

Embodiment 14. The daily women's health dietary supplement of any one of Embodiments 1 to 13, wherein the daily women's health dietary supplement is packaged in a transparent bottle.

Embodiment 15. The daily women's health dietary supplement of Embodiment 14, wherein the bottle comprises a scented insert.

Embodiment 16. The daily women's health dietary supplement of Embodiment 15, wherein the scented insert comprises a polymer and a scented oil.

Embodiment 17. The daily women's health dietary supplement of Embodiment 16, wherein the scented insert consists essentially of ethylene vinyl acetate and peppermint oil.

Embodiment 18. The daily women's health dietary supplement of any one of Embodiments 1 to 17, wherein each unit dose comprises:
between about 80 mcg to about 100 mcg vitamin K;
between about 1800 IU to about 2500 IU vitamin D;
between about 5 mcg to about 20 mcg vitamin B12;
between about 0.9 mg to about 1.1 mg boron;
between about 9 IU to about 15 IU of vitamin E;
between about 35 mg to about 65 mg magnesium;
between about 500 mcg to about 800 mcg of folate;
between about 7 mg to about 9 mg iron; and
between about 290 mg to about 350 mg of omega-3 fatty acids.

Embodiment 19. The daily women's health dietary supplement of any one of Embodiments 1 to 18, wherein the daily women's health dietary supplement comprises vitamin D3, vitamin K, boron, and magnesium, and:
the weight ratio of vitamin D3 to vitamin K is from about 0.045:0.099 to about 0.055:0.081;
the weight ratio of vitamin K to boron is from about 0.081:1.1 to about 0.099:0.9;
and the weight ratio of magnesium to boron is from about 45:1.1 to about 55:0.9.

What is claimed is:

1. A daily women's pre-natal supplement comprising a first capsule contained in a second capsule, wherein:
the first and second capsules are vegetarian;
the first capsule comprises aqueous-soluble nutrients in a solid and the second capsule comprises fat-soluble nutrients in an oil;
the aqueous-soluble nutrients consist of vitamin B12, biotin, choline, iron, iodine, calcium fructoborate, dimagnesium malate, and folate;
the fat-soluble nutrients consist of vitamin D3, vitamin E, vitamin K, and omega-3 fatty acids; and
the second capsule is an extended release capsule.

2. The daily women's pre-natal supplement of claim 1, wherein the weight ratio of vitamin B12 to vitamin K is from about 4:135 to about 12:45.

3. The daily women's pre-natal supplement of claim 1, wherein the weight ratio of vitamin B12 to folate is from about 4:900 to about 12:300.

4. The daily women's pre-natal supplement of claim 1, wherein the weight ratio of omega-3 fatty acids to dimagnesium malate is from about 160:75 to about 480:25.

5. The daily women's pre-natal supplement of claim 1, wherein the IU ratio of vitamin E to vitamin D3 is from about 5:3000 to about 15:1000.

6. The daily women's pre-natal supplement of claim 1, wherein the weight ratio of calcium fructoborate to dimagnesium malate is from about 0.5:75 to about 1.5:25.

7. The daily women's pre-natal supplement of claim 1, wherein the weight ratio of vitamin K to calcium fructoborate is from about 81:1250 to about 223.5:900.

8. The daily women's pre-natal supplement of claim 1, wherein:
the vitamin B12 is methylcobalamin,
the iron is ferrous bisglycinate,
the iodine is potassium iodide,
the folate is (6S)-5-methyltetrahydrofolate glucosamine salt
the vitamin K is menaquinone-7,
the vitamin D3 is cholecalciferol,
the vitamin E is α-tocopherol, and
the omega-3 fatty acid is docosahexaenoic acid.

9. The daily women's pre-natal supplement of claim 1, wherein:
the first capsule consists essentially of the vitamin B12 as methylcobalamin, the calcium fructoborate, the dimagnesium malate, the biotin, the choline, the iron as ferrous bisglycinate, the iodine as potassium iodide, the folate as (6S)-5-methyltetrahydrofolate glucosamine salt, cellulose, citric acid, corn starch, corn zein, tricalcium phosphate, lecithin, rice starch, and silica; and
the second capsule consists essentially of the vitamin K as menaquinone-7, the vitamin D3 as cholecalciferol, the vitamin E as α-tocopherols, an algal oil comprising the omega-3 fatty acids as docosahexaenoic acid, ascorbyl palmitate, d-alpha-tocopherol, coconut oil, silica, sunflower oil, and one or more odorant agents.

10. The daily women's pre-natal supplement of claim 1, wherein the daily women's pre-natal supplement is packaged in a transparent bottle.

11. The daily women's pre-natal supplement of claim 10, wherein the bottle comprises a scented insert.

12. The daily women's pre-natal supplement of claim 11, wherein the scented insert comprises a polymer and a scented oil.

13. The daily women's pre-natal supplement of claim 12, wherein the scented insert consists essentially of ethylene vinyl acetate and at least one citrus oil selected from the group consisting of grapefruit oil, lemon oil, and orange oil.

14. The daily women's pre-natal supplement of claim 1, wherein a unit dose of the aqueous-soluble nutrients and the fat-soluble nutrients is contained in two supplements, and wherein each unit dose comprises:
    between about 1000 IU to about 3000 IU vitamin D;
    between about 5 IU to about 15 IU vitamin E;
    between about 6 mcg to about 20 mcg vitamin B12;
    between about 12 mg to about 27 mg iron;
    between about 100 mcg to about 190 mcg iodine;
    between about 25 mg to about 75 mg dimagnesium malate;
    between about 290 mg to about 425 mg omega-3 fatty acids;
    between about 0.5 mg to about 1.5 mg calcium fructoborate;
    between about 67.6 mcg to about 126 mcg vitamin K; and
    between about 300 mcg to about 2600 mcg folate.

15. The daily women's pre-natal supplement of claim 1, wherein the user is a woman attempting to conceive.

16. The daily women's pre-natal supplement of claim 1, wherein the user is a woman is pregnant.

17. A daily women's post-natal supplement comprising a first capsule contained in a second capsule, wherein:
    the first capsule and the second capsule are vegetarian;
    the first capsule comprises aqueous-soluble nutrients in a solid and the second capsule comprises fat-soluble nutrients in an oil;
    the aqueous-soluble nutrients consist of vitamin B12, biotin, choline, iron, iodine, calcium fructoborate, dimagnesium malate, zinc, vitamin C, and folate;
    the first capsule further comprises an outer coating layer comprising zein;
    the fat-soluble nutrients consist of vitamin D3, vitamin E, vitamin K, and omega-3 fatty acids; and
    the second capsule is an extended release capsule.

18. The daily women's post-natal supplement of claim 17, wherein the weight ratio of vitamin B12 to vitamin K is from about 4:135 to about 12:45.

19. The daily women's post-natal supplement of claim 17, wherein the weight ratio of vitamin B12 to folate is from about 1:50 to about 1:10.

20. The daily women's post-natal supplement of claim 17, wherein the weight ratio of omega-3 fatty acids to dimagnesium malate is from about 160:75 to about 480:25.

21. The daily women's post-natal supplement of claim 17, wherein the IU ratio of vitamin E to vitamin D3 is from about 5:3000 to about 15:1000.

22. The daily women's post-natal supplement of claim 17, wherein the weight ratio of calcium fructoborate to dimagnesium malate is from about 0.5:75 to about 1.5:25.

23. The daily women's post-natal supplement of claim 17, wherein the weight ratio of vitamin K to calcium fructoborate is from about 81:1250 to about 223.5:900.

24. The daily women's post-natal supplement of claim 17, wherein:
    the vitamin B12 is methylcobalamin,
    the zinc is zinc bisglycinate,
    the iron is ferrous bisglycinate,
    the iodine is potassium iodide,
    the zinc is zinc bisglycinate,
    the folate (6S)-5-methyltetrahydrofolate glucosamine salt,
    the omega-3 fatty acid is docosahexaenoic acid;
    the vitamin K is menaquinone-7,
    the vitamin C as ascorbic acid;
    the vitamin D3 is cholecalciferol, and
    the vitamin E is α-tocopherol.

25. The daily women's post-natal supplement of claim 17, wherein:
    the first capsule consists essentially of the vitamin B12 as methylcobalamin, the calcium fructoborate, the dimagnesium malate, the biotin, the choline, the vitamin C as ascorbic acid, the zinc as zinc bisglycinate, the iron as ferrous bisglycinate, the iodine as potassium iodide, the folate as (6S)-5-methyltetrahydrofolate glucosamine salt, cellulose, citric acid, corn starch, corn zein, tricalcium phosphate, lecithin, rice starch, beta-carotene, and silica; and
    the second capsule consists essentially of the vitamin K as menaquinone-7, the vitamin D3 as cholecalciferol, the vitamin E as α-tocopherols, an algal oil comprising the omega-3 fatty acids as docosahexaenoic acid, ascorbyl palmitate, d-alpha-tocopherol, coconut oil, medium chain triglycerides, silica, sunflower oil, and one or more odorant agents.

26. The daily women's post-natal supplement of claim 17, wherein the daily women's post-natal supplement is packaged in a transparent bottle.

27. The daily women's post-natal supplement of claim 26, wherein the bottle comprises a scented insert.

28. The daily women's post-natal supplement of claim 27, wherein the scented insert comprises a polymer and a scented oil.

29. The daily women's post-natal supplement of claim 28, wherein the scented insert consists essentially of ethylene vinyl acetate and peppermint oil.

30. The daily women's post-natal supplement of claim 17, wherein a unit dose of the aqueous-soluble nutrients and the fat-soluble nutrients is contained in two supplements, and wherein each unit dose comprises:
    between about 1000 IU to about 3000 IU vitamin D;
    between about 5 IU to about 15 IU vitamin E;
    between about 6 mcg to about 20 mcg vitamin B12;
    between about 6 mg to about 20 mg iron;
    between about 50 mcg to about 250 mcg iodine;
    between about 25 mg to about 75 mg dimagnesium malate;
    between about 290 mg to about 425 mg omega-3 fatty acids;
    between about 0.5 mg to about 1.5 mg calcium fructoborate;
    between about 1500 IU to about 15,000 IU beta-carotene;
    between about 81 mcg to about 99 mcg vitamin K; and
    between about 300 mcg to about 2600 mcg folate.

31. The daily women's pre-natal supplement of claim 1, wherein the second capsule comprises hypromellose and gellan gum.

32. The daily women's post-natal supplement of claim 17, wherein the second capsule comprises hypromellose and gellan gum.

33. The daily women's post-natal supplement of claim 17, wherein the supplement further comprises provitamin A.

* * * * *